(12) United States Patent
Daunert et al.

(10) Patent No.: US 7,625,951 B2
(45) Date of Patent: Dec. 1, 2009

(54) STIMULI-RESPONSIVE HYDROGEL MICRODOMES INTEGRATED WITH GENETICALLY ENGINEERED PROTEINS FOR HIGH-THROUGHPUT SCREENING OF PHARMACEUTICALS

(75) Inventors: Sylvia Daunert, Lexington, KY (US); Sapna Kamlakar Deo, Lexington, KY (US); Jason Douglas Ehrick, Lexington, KY (US); Tyler William Browning, Lexington, KY (US); Leonidas G. Bachas, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 184 days.

(21) Appl. No.: 10/996,068

(22) Filed: Nov. 24, 2004

(65) Prior Publication Data

US 2005/0208469 A1    Sep. 22, 2005

Related U.S. Application Data

(63) Continuation-in-part of application No. 09/905,041, filed on Jul. 13, 2001, now abandoned.

(60) Provisional application No. 60/218,036, filed on Jul. 13, 2000.

(51) Int. Cl.
*B01D 21/01*    (2006.01)
*C09K 3/00*    (2006.01)

(52) U.S. Cl. .................................. 516/98; 516/70
(58) Field of Classification Search ........................ None
See application file for complete search history.

(56) References Cited

U.S. PATENT DOCUMENTS

| 5,384,118 | A | * | 1/1995 | LaValle ............... 424/70.13 |
| 5,502,082 | A | | 3/1996 | Unger et al. |
| 5,683,884 | A | | 11/1997 | Moore et al. |
| 5,707,815 | A | | 1/1998 | Charo et al. |
| 5,770,686 | A | | 6/1998 | Gallatin et al. |
| 6,469,055 | B2 | | 10/2002 | Lee et al. |
| 6,518,021 | B1 | | 2/2003 | Thastrup et al. |
| 2001/0036638 | A1 | | 11/2001 | Nolan et al. |
| 2002/0012943 | A1 | | 1/2002 | Fowlkes et al. |
| 2002/0068295 | A1 | | 6/2002 | Madou et al. |
| 2002/0192675 | A1 | | 12/2002 | Zauderer et al. |
| 2003/0124627 | A1 | | 7/2003 | Burmer et al. |
| 2003/0148264 | A1 | | 8/2003 | Held et al. |
| 2003/0161809 | A1 | | 8/2003 | Houston et al. |
| 2003/0166160 | A1 | | 9/2003 | Hawley et al. |
| 2003/0232340 | A1 | | 12/2003 | Anderson |
| 2003/0232383 | A1 | | 12/2003 | Daunert et al. |
| 2004/0038217 | A1 | | 2/2004 | Yang |
| 2004/0038306 | A1 | | 2/2004 | Agnew et al. |

FOREIGN PATENT DOCUMENTS

| EP | 1 199 564 B1 | 4/2002 |
| WO | WO 00/08151 | 2/2000 |
| WO | WO 02/085388 A1 | 10/2002 |

OTHER PUBLICATIONS

Ngo et al., in The Protein Folding Problem and Tertiary Structure Prediction, 1994, Merz et al. (ed.), Birkhauser, Boston, MA, pp. 433 and 492-495.*
Beebe et al., Functional hydrogel structures for autonomous flow control inside microfluidic channels, Nature, Apr. 2000, vol. 404, p. 588-590.*
Veluthambi et al., Calcium- and Calmodulin-regulated phosphorylation of soluble and membrane proteins from corn coleoptiles, Plant Physiol. (1984) 76(10): 359-365.*
Merriam Webster's Collegiate Dictionary, 10th ed., 1993, Massachusetts, Merriam-Webster, Incorporated, p. 317.*
Retrieved from the Internet <URL: http://www.dfrc.ars.usda.gov/RS95_pdfs/pnr.pdf>.*
Roberts et al. (Biochemistry, 1985, 24, pp. 5090-5098).*
Medline search result, Retrieved from the Internet <URL: http://www.ncbi.nlm.nih.gov/sites/entrez>.*
Medline search result, Retrieved from the Internet <URL: http://www.ncbi.nlm.nih.gov/sites/entrez>, [Retrieved in 2008].*
Retrived from the Internet <URL: http://www.dfrc.ars.usda.gov/RS95_pdfs/pnr.pdf>, [Retrieved in 2008].*
Miyata, Takashi., et al. "A reversibly antigen-responsive hydrogel." Nature, vol. 399; Jun. 24, 1999, pp. 766-769.
Serpe. Michael J., et al. "Colloidal Hydrogel Microlenses." Adv. Mater. 2004, 16, No. 2, Jan. 16, 2004, pp. 184-187.

* cited by examiner

*Primary Examiner*—Suzanne M. Noakes
*Assistant Examiner*—Jae W Lee
(74) *Attorney, Agent, or Firm*—McDermott Will & Emery LLP

(57) ABSTRACT

A hydrogel microdome that can swell in response to a stimuli or target molecule is formed by polymerizing a mixture comprising a monomer capable of forming a hydrogel with a biopolymer. An array of hydrogel microdomes can be formed on a substrate by microspotting the mixture and polymerizing. The array can be used for high-throughput screening of analytes as well as for use as an actuator and biosensor using the swelling property of the hydrogel.

6 Claims, 12 Drawing Sheets a          b          c

FIG. 9
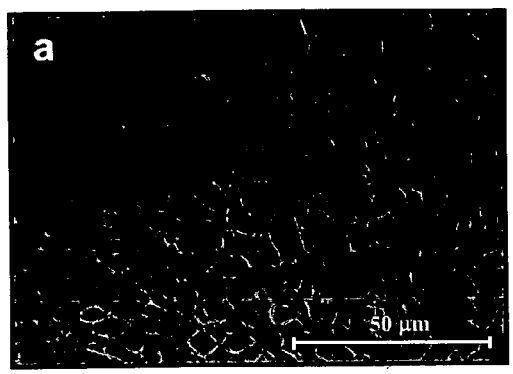
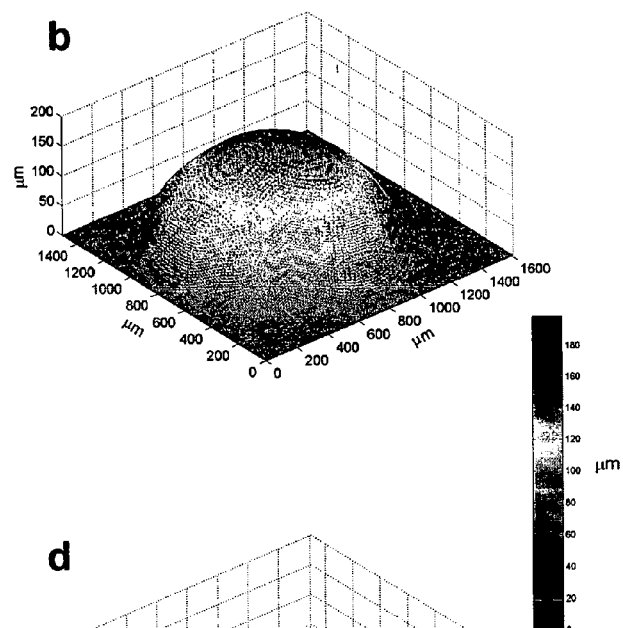
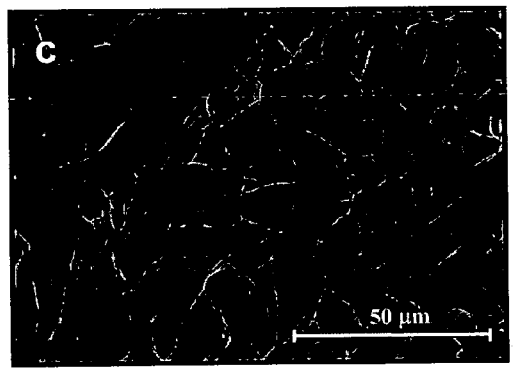
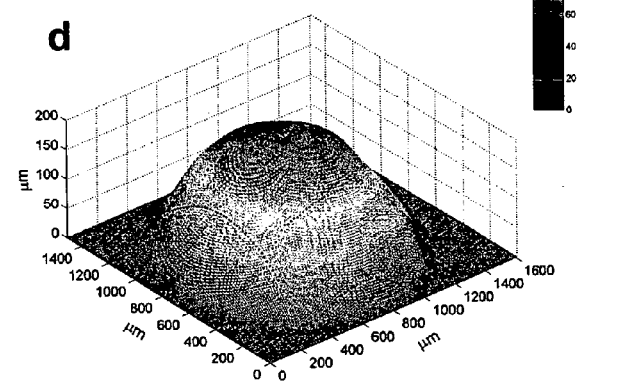

Original State      Swollen State

FIG. 15
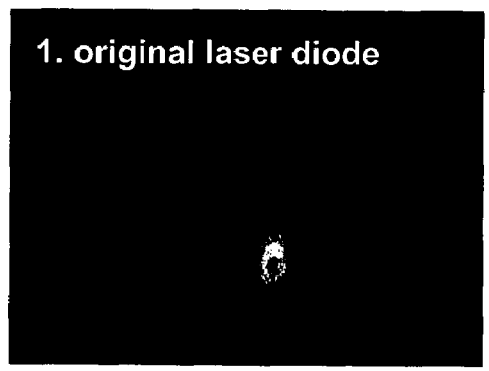
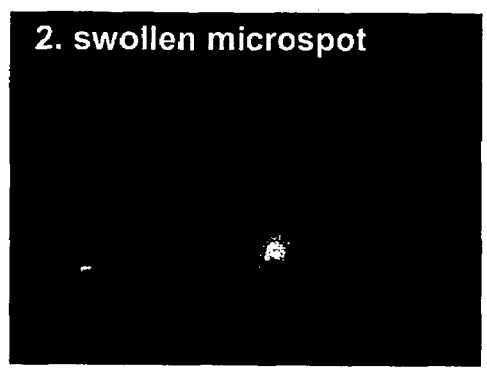
FIG. 16
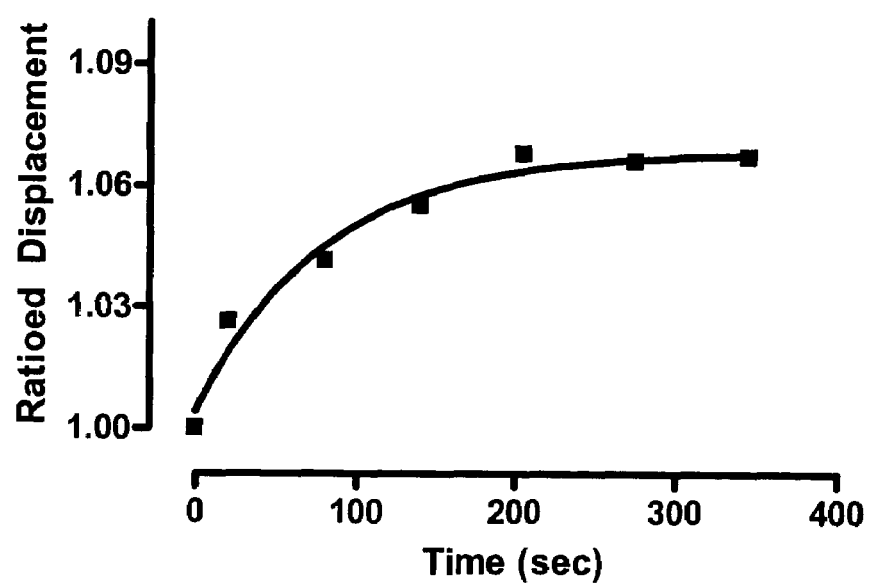

STIMULI-RESPONSIVE HYDROGEL MICRODOMES INTEGRATED WITH GENETICALLY ENGINEERED PROTEINS FOR HIGH-THROUGHPUT SCREENING OF PHARMACEUTICALS

CROSS-REFERENCE TO RELATED APPLICATIONS

This application is a continuation-in-part of application Ser. No. 09/905,041 filed Jul. 13, 2001, published Jun. 6, 2002 as Publication No. US 2002/0068295, now abandoned which claims priority to U.S. Provisional Application Ser. No. 60/218,036, filed Jul. 13, 2000, which is incorporated herein by reference.

GOVERNMENT INTEREST IN THE INVENTION

This invention was made with Government support under Grant No. EB003072 awarded by the National Institutes of Health. The Government may have certain rights in this invention.

FIELD OF THE INVENTION

This invention is directed to a stimuli-responsive hydrogels integrated with genetically engineered proteins for use for high-throughput screening of analytes as well as for use as an actuator and biosensor.

BACKGROUND OF THE INVENTION

Proteins and DNA are information rich molecules with structural and electrical properties which make their incorporation into the human manufacturing arsenal an attractive proposition. Several microstructures using oligonucleotides as building blocs have been demonstrated (N. C. Seeman, *Ann. Rev. Biophys. Biomol. Struc.*, vol. 27, pp. 225, 1998; B. Winfree, F. Liu, L. Wenzler, and N. C. Seeman, *Nature*, vol. 394, pp. 539, 1998.), and many particles/objects have been derivatized with DNA strands or oligonucleotides (R. Bashir, "DNA-Mediated Artificial Nano-Bio-Structures: State of the Art Future Directions," *Superlattice and Microstructures*, vol. 29, pp. 1-16, 2001.) Short strands of DNA, also known as aptamers have been suggested as a tool in DNA mediated self assembly of micro components into larger subassemblies or onto a PC board (C. F. Edman, C. Gurtner, R. E. Formosa, J. J. Coleman, and M. J. Heller, "Electric-Field-Directed Pick-and-Place Assembly," *HDI*, vol. October, pp. 30-35, 2000; C. F. Edman, R. B. Swint, C. Gurtner, R. B. Formosa, S. D. Roh, K. B. Lee, P. D. Swanson, D. B. Ackley, J. J. Coleman, and M. J. Heller, "Electric Field Directed Assembly of an InGaAs LED onto Silicon Circuitry," *IEEE Photonics Tech. Lett.*, vol. 12, pp. 1198-1200, 2000; C. A. Mirkin, R. L. Letsinger, R. C. Mucic, and J. J. Storhoff, *Nature*, vol. 382, pp. 607, 1996.). Proteins have also been used in a wide variety of microstructures with motor proteins, perhaps the most studied example. The first examples of combinations of proteins with micromachined structures were realized recently.

The combination of the natural biopolymers with microelectromechanical systems (MEMS) and nanoelectromechanical systems (NEMS) promises the advent of a totally new class of sensors and actuators with applications in drug delivery, diagnostics, biocompatible surfaces, prosthetics and many other fields.

Advanced biomaterials are of high importance in biomedicine, and especially, in new-generation medical devices and implants. These materials can be used in a multitude of biomedical applications related to the treatment and management of disease. Currently, there are a limited number of biomaterials that are suitable for biomedical applications. For example, the materials need to be prepared and perform in a reproducible, accurate, selective, and sensitive manner, and they need to be amenable to integration into devices that can be employed in a variety of applications (e.g., biosensors, delivery systems, diagnostic and high throughput screening platforms, etc.), those being in vitro or in vivo.

Conventional drug delivery methods incorporate tablets, capsules, and emulsions that have difficult-to-control release rates and nonspecific delivery sites. An ideal drug delivery system would be able to provide a specific release profile in response to an external stimulus. Traditional drug release tablets cannot control the amount of drug released efficiently. The drug concentration may extend beyond the therapeutic window risking ineffectiveness or toxicity. Over the last two decades a new type of drug delivery, controlled drug delivery (also referred to as controlled release), has evolved in order to optimize drug therapy when conventional drug delivery methods, such as tablets, pills, solutions, and suspensions, are inadequate. Controlled release is most commonly achieved by incorporating (or "encapsulating") drugs in either biodegradable or nondegradable polymers, which can control the release of the drug to the body over specific times ranging from a day to several years. A major limitation in the usefulness of controlled release systems is that conventional implantable devices release drugs at a predetermined rate(s). However, in certain instances, it is required that drugs are administered either at a life-threatening moment or repeatedly at a certain critical time of day. The latter is a requirement in the design of controlled release systems for certain disease states, such as diabetes, heart disease, and hormonal disorders. Drug delivery technology could be brought to the next level if we could understand how to prepare "intelligent" polymers that are "responsive" to the patient's therapeutic requirements and deliver certain amount of a drug in response to a biological stimulus.

A multitude of binding proteins exist for a variety of ligands such as sugars, amino acids, peptides, and inorganic ions. Likewise, enzymes are another class of proteins that undergo conformational changes as they catalyze a specific reaction. Enzymes can serve as biorecognition elements for substrates, inhibitors, and allosteric effectors. These binding proteins and enzymes come from a range of organisms, some of which grow under extreme environmental conditions. These organisms, termed extremophiles, have adapted to prosper at temperatures as high as that of boiling water in thermal vents (hyperthermophiles) or as low as that of icebergs (psychrophiles). Unlike conventional of-the-shelf proteins that come from organisms that grow at 20 to 37° C., and are non-functional at temperatures above or below this range, proteins from extremophiles can perform under severe conditions.

There are a few examples in the literature where proteins have been integrated into materials capable of displaying a significant change in their characteristics in response to a stimulus. Most of these examples refer to the development of what are known as "smart" polymers or devices intended for use in delivery systems. The "smart" polymers can be prepared so that they are responsive to the individual patient's therapeutic requirements and deliver certain amount of a drug in response to a biological stimulus.

The conventional "smart" polymer based on antigen-antibody interactions showed promise for responsive drug delivery. A semi-interpenetrating hydrogel polymer network was prepared consisting of a polymer containing rabbit antibody (IgG) and goat anti-rabbit IgG as the antigen. This hydrogel is able to swell in the presence of free antigen, rabbit IgG, due to competition between free antigen and polymer-immobilized antigen. Upon removal of free antigen, the hydrogel shrinks, thus, exhibiting a reversible swelling and shrinking behavior, which was dependent on free antigen concentration.

There is a need for high-throughput screening devices in the pharmaceutical industry for rapid and accurate selection of possible drug candidates that are most active or effective. Currently, laborious combinatorial techniques are used to screen analytes. These techniques are taxing on both time and resources. Utilizing a stimuli-responsive hydrogel array of microdomes of the present invention, allows for efficient screening of these compounds in minutes.

This invention is directed to a highly sensitive responsive system for detecting analytes based on the induced conformational change upon binding of the analytes to their respective binding proteins. The system can also be useful as an actuator or biosensor. The conventional hydrogel synthesis does not permit exact control of three-dimensional structure of the hydrogel microdome, making it difficult to predict hydrogel performance and hindering the potential for biomedical applications. To overcome this problem, this invention includes the preparation of a hybrid hydrogel that incorporates a biopolymer within its structure. The biopolymer can be a monomer or multimer. This hybrid hydrogel has precise and reproducible swelling characteristics.

SUMMARY OF THE INVENTION

The present invention provides for a stimuli-responsive hydrogel network integrating a biopolymer. The hydrogel network can be formed into microdomes that undergo a phase transition. In response to a stimulus or the presence of an analyte, the hydrogel microdome swells. The hydrogel microdome can then undergo a reversible swelling of the network in response to an external stimulus.

The stimuli-responsive hydrogels of the present invention have an integrated biological recognition element that provides excellent selectivity for ligands of interest. The stimuli-sensitive hydrogels reproducibly swell upon addition of a target molecule, which controls the release of a biomolecule. The amount of swelling of these hydrogels was attributed to release of non-covalent bonds within the polymer network.

The stimuli-responsive hydrogel of the present invention has a multiple ligand response with precise three-stage active swelling characteristics achieved by coupling ligand sensing with the conformational change of the site-specifically immobilized biological recognition element. In addition, the extent of actuation observed is proportional to the concentration of ligand present.

The stimuli-responsive hydrogels of the present invention are useful for high-throughput screening of analytes as well as for use as an actuator or a biosensor.

BRIEF DESCRIPTION OF THE DRAWINGS

The present invention may be more readily understood by reference to the following drawings wherein:

FIG. 9 shows SEM images (a) and (c) depicting calmodulin protein-integrated hydrogel in the original (shrunken) and swollen states, respectively, (b) and (d) shows the corresponding ellipsoid surface maps of microdomes (a) and (c), respectively, formed of a calmodulin protein integrated hydrogel;

FIG. 15 are images of the light diffraction pattern off the unswollen microdome and the interference pattern generated off a swollen microdome;

FIG. 16 graphically illustrates the swelling kinetics of the hydrogel microdomes;

DETAILED DESCRIPTION OF THE INVENTION

This invention is directed to a stimuli-responsive hydrogel that can be used as used as a high-throughput screening device of analytes and pharmaceuticals. The hydrogel is in the form of microdomes comprising a hydrogel having integrated therein, genetically engineered proteins. In particular, the stimuli-responsive hydrogel has a three dimensional open cell lattice structure that integrates a biological recognition element and a biomolecule ligand.

Figure 1:
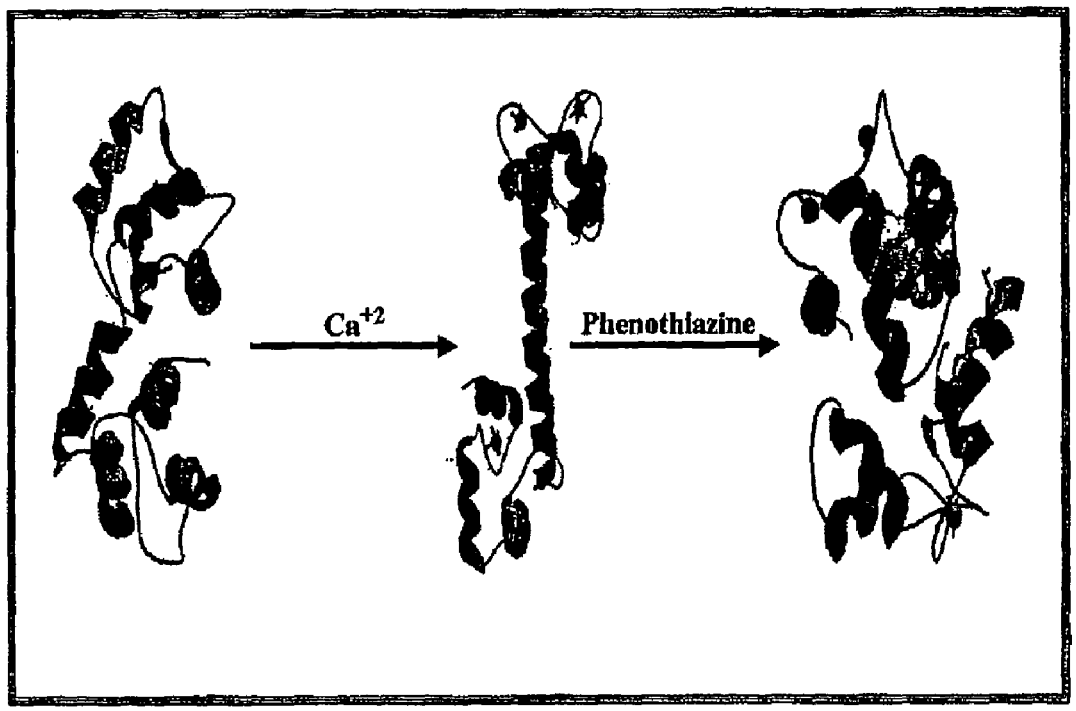
FIG. 1 is an illustration of calmodulin undergoing a conformational change when it binds to $Ca^{++}$ and phenothiazine.

A fine-tuned response is achieved by creating three specific swelling stages of the protein-integrated hydrogel, which offers added control over the conventional two-stage hydrogel swelling illustrated in FIG. 1. In particular, the stimuli-responsive hydrogel of the present invention has integrated therein a biopolymer that produces a response in the presence of a protein-binding ligand. The biopolymer can be a monomer or multimer. The response of the stimuli-sensitive hydrogel is a direct result of specific binding events and concomitant conformational changes of the integrated protein occurring simultaneously within the hydrogel. The advanced biomaterials have tailored response characteristics.

Micromechanical devices and biosensors, such as MEMS and NEMS, i.e., systems that comprise a machined microstructure or nanostructure, respectively, such as for example a chip comprising a polysilicon membrane for pressure sensing, contain the multimeric biopolymers of the present invention. Such devices can comprise a hydrogel or a redox polymer. The device further comprises both a redox polymer and a hydrogel. MEMS and NEMS systems further comprise an electronic component which may either be part of the microstructure or nanostructure or in hybrid fashion coupled thereto.

As used herein, the term "hydrogel" refers to a polymer that takes on at least 30% of its weight in water.

As used herein the term "sensor" or "biosensor" refers to a multimeric biopolymer which gives off a detectable signal, such as for example, a fluorescent signal in response to an analyte or the swelling response of a hydrogel.

As used herein the term "actuator" refers to a multimeric biopolymer that (a) exhibits a mechanical response when exposed to an analyte or (b) causes another substance, such as for example a hydrogel, to exhibit a mechanical response when the multimeric biopolymer is exposed to an analyte.

As used herein the term "biopolymer" refers to a biomolecule capable of responding to a change in its microenvironment. Examples of biopolymers are proteins, polypeptides, and nucleic acid molecules. One way in which a biopolymer can respond to a change in its microenvironment is by changing its conformation. For example, one way in which a protein can change conformation is by unfolding, totally or in part (i.e., local areas of the protein can unfold). Examples of microenvironmental changes that can cause the biopolymers to respond include such things as an increase or decrease in pH or an increase or decrease in the concentration of specific analyte(s). One specific example of a biopolymer is calmodulin (CaM). The specific analyte bound by CaM are calcium ions and the anti-psychotic phenothiazine class of drugs, which include chlorpromazine, trioridazine, trifluoperazine and perphenazine. CaM molecules respond to binding calcium by changing conformation. In addition, when phenothiazines are present, CaM responds by undergoing additional change in conformation.

In one aspect, a synthetic multimeric biopolymer can comprise at least two, preferably a plurality, of monomeric units of a biopolymer. At least one of the monomeric units, and preferably a plurality of the monomeric units, comprise one or more binding regions that bind to an analyte or a pharmaceutical compound. The analyte may be a biochemical that is found in an organism (e.g., bacteria, yeast, animals, humans, plants, etc.), such as for example a sugar, a protein, a nucleic acid, a hormone, a vitamin, or a co-factor. The analyte may also be an ion such as for example a hydrogen ion, a hydroxyl ion, an oxyanion (e.g., phosphate, sulfate, etc.) or a cation (e.g., calcium ion, etc.). The bonds that form between the analyte and the binding region include all chemical bonds except covalent bonds. Examples of such chemical bonds are ionic bonds, hydrogen bonds, hydrophobic interactions and van der Waals forces. Further, the analyte may be molecules such as drugs, vitamins, hormones, antibodies, enzymes, co-factors, nucleotides, proteins and so forth.

The monomeric unit is selected from the group consisting of a full-length protein, a polypeptide which is a fragment of a full-length protein, a nucleic acid molecule, which is preferably an aptamer, a peptide nucleic acid. The monomeric units may be the same or different.

The multimeric polymer undergoes a detectable conformational change in response to exposure to the analyte. Such a composition is a structurally linked multimer of biomolecules (e.g., multimers composed of linked proteins, DNA, RNA, peptide nucleic acids, etc.), and combinations thereof. When disposed within a device, such as for example a polymeric drug delivery device or a machined microstructure or nanostructure, the conformationally-reactive multimeric biopolymer can be used to open or close a channel, either directly or indirectly. As used herein, this response to the analyte is referred to as an actuating event.

Exposure of the multimeric biopolymer to the analyte causes the multimeric biopolymer to emit a detectable signal, such as for example a fluorescent signal. Examples of such detectable signals are fluorescent signals, an optical signals, electrochemical signals, pressure changes, changes in dielectric constant, mass changes, volume changes, and temperature changes. Such multimeric biopolymers can be used as a sensor, particularly within a MEMS or NEMS to detect the presence of the analyte and to generate a signal which is transmitted to a transducer.

Figure 2:
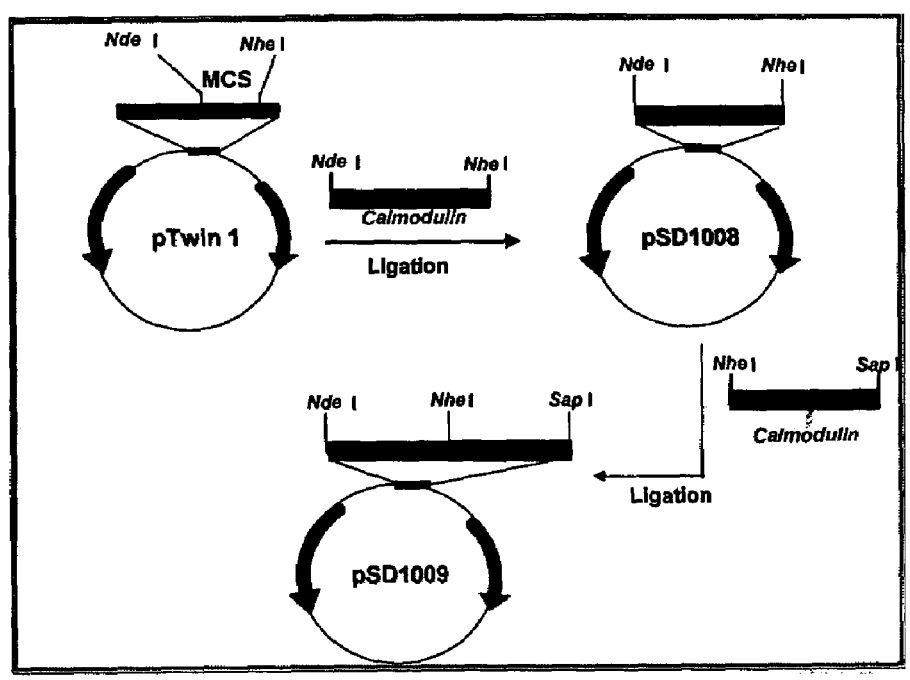
FIG. 2 shows the construction of plasmid pSD1009 in the preparation of a dimer of calmodulin.

An example of a multimeric biopolymer of the present invention is a dimer of the CaM protein. The CaM dimer comprises a protein where the C-terminal end of one CaM molecule is attached to the N-terminal end of an adjacent calmodulin molecule. To construct the protein dimmer, two sets of polymerase chain reaction (PCR) reactions are performed. To amplify the CaM gene, primers are designed such that they code for NheI and SapI endonuclease site at the 5' and 3' end for one CaM gene and NdeI and Nhe I site for the other CaM gene. As illustrated in FIG. 2, the two fragments will be then individually ligated into plasmid pTwin1. This expression vector contains the sequence for the cellulose-binding domain, which allows affinity purification of the fusion protein. The CaM dimer is expressed and purified. Two types of CaM dimers were constructed, one containing a unique cysteine at the C-terminus and the other containing two cysteines one at each terminus. Dimers of other proteins can be prepared in an analogous manner.

Figure 3:
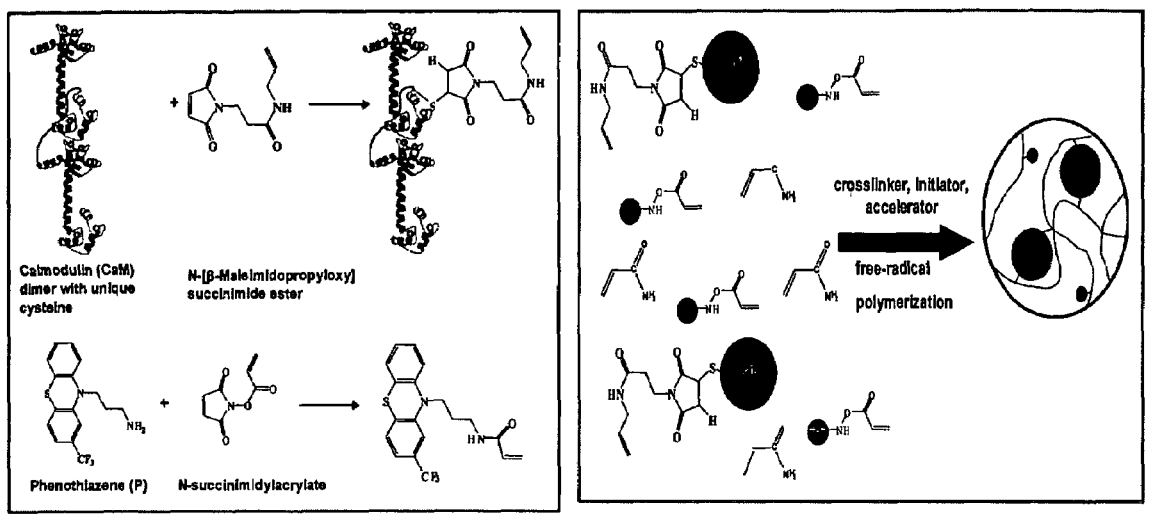
FIG. 3 illustrates the modification of calmodulin and a phenothiazine, and the synthesis of a protein hydrogel.

Using a heterobifunctional linker containing maleimide and succinimide groups, an allyamine is attached to the CaM dimer. Similar chemistry can be performed to modify a phenothiazine derivative containing a free amino group with N-succinimidylacrylate. As illustrated in FIG. 3, using modified CaM, the phenothiazine derivative, and the acrylamide-bisacrylamide couple, smart hydrogel polymer material can be synthesized by free radical polymerization. In the case of the CaM dimer with two cysteines, smart material can be synthesized using modified CaM without the phenothiazine derivative. The hydrogel can be synthesized with different dimensions.

CaM undergoes a hinge-type motion upon binding to calcium. CaM consists of two domains, the N- and the C-domain. Two high affinity calcium-binding sites are located in the C-domain and the other two low affinity calcium-binding sites are located in the N-domain. As illustrated in FIG. 1, upon binding to calcium, CaM undergoes a change in conformation, which exposes two hydrophobic pockets located in the N- and C-domains. Certain hydrophobic peptides and the anti-psychotic phenothiazine class of drugs interact with these exposed hydrophobic pockets.

Like the monomeric units, the multimeric biopolymers change their conformation in response to the microenvironment. In fact, changes in multimeric biopolymers in response to a particular microenvironmental change are greater in magnitude than are changes in monomeric units that comprise the multimeric biopolymer that are caused by the same microenvironmental change. For example, the conformational change induced in the CaM dimer is greater in magnitude than the conformational change induced in a separately tested, single CaM molecule in response to calcium binding. Such changes in multimeric biopolymers, therefore, can be additive or even greater than additive, compared to the changes in the monomeric units that comprise the biopolymer, in response to the same microenvironment.

Multimeric Proteins and Polypeptides

The multimeric proteins and polypeptides comprise at least two, preferably from 2 to 10 proteins or polypeptides. At least one, preferably a plurality, of the monomeric units of the multimeric protein comprise a binding region for an analyte. The monomeric units of the multimeric proteins and polypeptides may be the same or different. For example, the multimeric protein may be comprised of a single protein. Alternatively, the multimeric protein may comprise a structural protein which changes its conformation in response to contact with an analyte and an enzyme which catalyzes a chemical reaction with its specific substrate. Catalysis of such reaction results in release of protons or removal protons from the microenvironment of the multimeric protein.

In certain instances, the conformationally-reactive multimeric proteins are designed to undergo a change in response to binding of a specific biochemical to the binding site or sites in the multimeric protein. In other instances, the conformationally-reactive multimeric proteins of the present invention are designed to undergo a change in conformation in response to a change in ion concentration, particularly a change in hydrogen ion or hydroxide concentration. For example, ion concentration changes above or below the isoelectric point of the protein will cause the protein to change its three-dimensional shape.

The multimeric proteins may comprise a plurality of one or more structural proteins that undergo a conformational change in response to binding to an analyte. Alternatively, the multimeric proteins may comprise a plurality of enzymes linked to or in close proximity to a plurality of structural proteins. Upon binding to their respective substrates, the enzymes catalyze a reaction that leads to a change in pH in the microenvironment surrounding the structural protein thereby causing a change in conformation of the structural proteins.

Methods for preparing multimers of proteins are known in the art and a variety of methods exist. In one method, sulfhydryl groups present in cysteine amino acids of different proteins are used to create covalent bonds between the separate proteins. This is done through formation of disulfide bonds between the cysteines in the different proteins. Such disulfide bond formation occurs under oxidative conditions, i.e., atmospheric oxygen catalyzes formation of the disulfide bonds. In using this method of forming protein multimers, care must be taken to ensure that the cysteines involved in formation of the disulfide bonds will not affect the structure or function of the protein in an adverse way.

In addition to crosslinking through disulfide bond formation, other methods of chemical crosslinking of proteins to one another exist. For example, this can be achieved by either using directly reactive groups on the protein (e.g., amines, carboxylic groups, etc.) or by creating reactive groups on the protein (e.g., in the case of glycosylated proteins the sugars are oxidized to from aldehydes, acids, etc.). Once reactive groups on the protein exist, then they are directly reacted with the next protein or they are connected to the next protein via commercially available mono- or bifunctional linkers by following well-established protocols.

Other approaches to making protein multimers involve manipulation of the genes encoding such proteins. After manipulation, the genes are used to produce the proteins. Such proteins may be multimeric proteins or may be proteins that are then crosslinked to one another, as described above.

For example, in one instance, genes encoding proteins (the same protein or different ones, depending on the chosen application) can be fused together, end-to-end or start-to-end from their N- and C-termini, using recombinant DNA techniques. In such method, plasmids are constructed that incorporate the gene of the designed chosen multimer protein. The plasmids are inserted into bacterial, yeast, or mammalian vectors. The proteins are then expressed and purified using established molecular biology protocols.

Such recombinant DNA techniques can also be used to produce the monomeric subunits of what is to become the protein multimer. In such method, site-directed mutagenesis is used to remove or create unique amino acids in the protein monomer that facilitate attachment of one protein to another. Such site-directed mutagenesis techniques are well known to those skilled in the art. For example, such method can be used to introduce cysteine amino acids into the protein monomers. When the manipulated gene is then used to produce the proteins, such proteins can then readily be crosslinked to one another, as described above. Such techniques are described in U.S. Pat. Nos. 4,132,746 and 4,187,852.

Conformational changes in multimeric proteins can be detected using techniques such as NMR and X-ray crystallography. Several biosensing systems have been developed in which a fluorophore is attached to a unique site in the protein (Salins, L. L. E., Schauer-Vukasinovic, V., Daunert, S. SPIE-Int. Soc. Opt. Eng. 1998, 3115 16-24; Schauer-Vukasinovic, V. Cullen, L., Daunert, S. J Am. Chem. Soc., 1997, 119, 11102-11103; Wenner, B. R. Douglass, P. M., Shrestha, S., Sharma, B. V., Lai, S., Madou, M. J., Daunert, S. Proceedings of SPIE, 2, 59-70, 2001; L. L. E. Salins, C. Mark Ensor, R. Ware, and S. Daunert, Anal. Biochem., in press, 2001). The change in conformation in the presence of a ligand is then monitored by measuring a change in fluorescence of the reporter fluorophore.

The multimeric proteins are dimers, trimers, and multimers of the same protein or of combinations of two or more different proteins forming a polymer. The genetically engineered polymer proteins can be used as sensors/actuators in a variety of applications that range from biosensors to responsive drug delivery systems to molecular machines. Therefore, we envision applications in environmental analysis, and in the diagnostics, biotechnology, and pharmaceutical industries.

Multimeric Nucleic Acids

The multimeric biopolymers can also be nucleic acid molecules, such as DNA or RNA. As for multimeric proteins, described above, the nucleic acid multimers comprise repeating units of two or more smaller, monomeric molecules. Such monomeric units may be the same or different. Such monomers, as well as the multimeric nucleic acid, are able to respond to the presence of an analyte.

One such type of nucleic acid monomer that can be used to make multimeric nucleic acids is called an oligonucleotide ligand or "aptamer." Aptamers are single-stranded DNA or RNA molecules that bind with high affinity to specific target or analyte molecules. Such analyte molecules can be drugs, vitamins, hormones, antibodies, enzymes, co-factors, nucleotides, proteins and so forth. Aptamers can range from between 8 to 120 or more nucleotides in length. Within this nucleotide sequence is contained a minimal sequence needed for binding to the analyte. Such sequence is normally between 15 to 50 nucleotides in length. Aptamers undergo a conformational change after binding of specific analytes. The binding constant of aptamers to their specific analyte molecules ranges from micromolar to sub-nanomolar ranges.

Aptamers have a number of advantages over other molecules that specifically bind target molecules. Aptamers have remarkable specificity for their specific analytes. Aptamers can discriminate between analytes based on subtle differences in the analytes. For example, aptamers can discriminate between analytes based on the presence or absence of a methyl or hydroxyl group. Aptamers can discriminate between analytes based on the difference between the D- and L-enantiomer.

Another advantage of aptamers is that their synthesis is straightforward. Aptamers are produced by chemical synthesis, which is extremely accurate and reproducible. Aptamers produced by such synthesis can be purified, under denaturing conditions, to a high degree. Reporter molecules, fluorophores for example, can subsequently be easily attached to purified aptamers. Such attached fluorophores can emit a fluorescence signal whose intensity varies depending on whether the aptamer has or has not bound its target analyte. Such differential emission of fluorescence in response to target binding can facilitate the use of such labeled aptamers as sensors and actuators.

Aptamers that bind selectively to a specific analyte are commonly selected from very large random sequence oligonucleotide libraries comprised of as many as $10^{15}$ random sequences (McGown, et al., 1995, Anal Chem, 67:663A-68A; Jayasena, 1999, Clin Chem, 45:1628-50). Such selection involves an iterative enrichment process. Such process is called SELEX (systematic evolution of ligands by exponential enrichment). Steps in the SELEX process involve passing the entire oligonucleotide library over a support, such as an affinity column, to which the analyte molecule is attached. The oligonucleotides that do not bind to the analyte in the column pass through the column and are discarded. The oligonucleotides that bind to the analyte are then eluted from the column. The oligonucleotides that elute from the column are then amplified using the PCR. The PCR-amplified pool of oligonucleotides is then passed over the column again, as described above, and the eluate is again amplified by PCR. The cycle is repeated numerous times. Commonly, the cycle is repeated anywhere from between 8 to 15 times.

Once aptamers are obtained, polymers of the aptamers are prepared. Such polymeric aptamers can be prepared by employing several strategies. For example, DNA synthesizers can be used to prepare a DNA segment that terminates in a functional chemical group (e.g., thiol, biotin, etc.). This allows for coupling of the DNA aptamer unit to form dimers, trimers, etc. of the original aptamer.

In another embodiment, the conformationally reactive multimeric biopolymers are aptamers, which are nucleic acid ligands composed of single strands of DNA or RNA. These are molecular recognition elements that upon binding to their respective ligands (e.g., drugs, vitamins, hormones, antibodies, enzymes, biological co-factors, etc.) undergo a conformational change. The binding constant of aptamers to their respective ligands ranges from µM to sub-nM, making them suitable for detection of biomolecules in biological fluids. The three-dimensional structure of a functional aptamer can be denatured by temperature, pH, salt gradient, metal ions, and electrochemical potential. Thus, aptamers can be used in a similar fashion to the binding proteins mentioned above. Specifically, polymeric aptamers can be prepared by employing several strategies. For example, DNA synthesizers can be used to prepare a DNA segment that terminates in a functional chemical group (e.g., thiol, biotin, etc.). This allows for coupling of the DNA aptamer unit to form dimers, trimers, etc. of the original aptamer. Thiol-terminated aptamers can be coupled to each other by formation of disulfide bonds (connecting unit between two aptamers) under oxidizing conditions. In the case of biotin-terminated aptamers the connecting units can be avidin, streptavidin, or anti-biotin antibodies, for example. Avidin or streptavidin bind to up to four biotinylated compounds, which allows for organization of the aptamers in networks that are three-dimensionally different from those assembled by employing antibodies as connectors. Polymeric RNA aptamers can be prepared in a similar fashion.

Redox Polymers

The multimeric biopolymers are useful if the changes (e.g., conformational change) that they undergo in response to the microenvironment (e.g., binding of an analyte) are reversible. Reversibility allows the inventions of which the multimeric biopolymers are a component to be used more than once. That is, once the multimeric biopolymer binds its specific analyte and, for example, causes swelling and shrinking of a hydrogel, it would be advantageous if the multimeric biopolymer could be returned to its original state, for example the state in which no analyte is bound by the multimeric biopolymer.

One way in which the changes the multimeric biopolymers undergo can be reversed is through the use of redox polymers. Redox polymers are polymers, such as polypyrrole, polyaniline, polythiophene and the like, that are sensitive to pH, applied potential and chemical potential in their microenvironment. The redox polymers are electronically conducting polymers. Such redox polymers, can conduct a current that originates from an electrode, for example, and when the redox polymer is in contact or close proximity to the multimeric biopolymers, can reverse the changes that occurred in the multimeric biopolymer, by analyte binding, for example. In such case, the invention can be viewed as a "molecular gate" wherein the multimeric biopolymer opens or closes in response to analyte binding and wherein the redox polymer acts to override this process.

The Redox polymer device which employs the multimeric biopolymer can be used as a molecular gate or actuator to regulate the flow of molecules, such as drugs, heparin, bioactivators, and ions through a channel or an opening in the device.

An example of the manner in which conformational changes of multimeric biopolymers may be utilized in conjunction with MEMS and NEMS is that of the incorporation of the multimeric biopolymers within channels of a substrate. These channels could, for example, be connected to a drug delivery chamber on one side. Opening and closing of the channels is accomplished by changing the conformation of the multimeric polymers. For example, in those cases where the biopolymer contains ligand-binding proteins (examples include binding proteins, receptors, enzymes, etc.), the conformational change occurs when the ligand binds to the protein.

The multimeric biopolymer may be attached to the channel surface, for example by a covalent bond. Alternatively, the multimeric biopolymer may be in a solution or suspension which is disposed within the porous substrate. Depending on the conformation of the biopolymer, the pores will be open or closed.

The device may be a MEMS or NEMS structure. Such structures are top-down machined devices with dimensions in the micrometer respectively nanometer range. They typically involve semiconductor industry type manufacturing methods. Products include pressure sensors, valves, pumps, accelerometers, gyros, etc. With the ever decreasing dimensions of the lithography written features there is now an overlap between features that can be made with top-down methods and bottom-up methods (the ones described above to make the multimeric biopolymer sensors/actuators). This size overlap presents many new product opportunities. For example MEMS and NEMS structures may be manipulated by multimeric biopolymers. In such an embodiment, the multimeric biopolymer directly opens and closes the channel.

In a further embodiment the multimeric biopolymer is attached to or in communication with a movable door that is comprised of a rigid substance, such as for example silicon, or a hydrogel. The change in conformation that is initiated by binding of the analyte to the multimeric biopolymer causes the door to move, thereby opening or closing the channel. Such devices may further comprise a redox polymer which is blended with the multimeric biopolymer as described below.

Once the polymer proteins are prepared, they preferably are coupled to the surface of the substrate. As is the case with the attachment of oligonucleotides to these surfaces, there are numerous well-established protocols for the successful attachment of proteins to surfaces. To limit loss of function or collapse of the three-dimensional structure of the multimeric biopolymer, hydrophilic surfaces are chosen.

Direct immobilization of the multimeric protein to the surface can be attained by reacting an amino acid on the protein with the surface itself or by disposing a coating with reactive groups on the channel surface. Different amino acids in a protein biopolymer structure are used for covalent attachment. For example, the most common method of attachment of proteins to surfaces is through the amine groups of lysine residues. The thiol groups of cysteine molecules, as well as the carboxylic groups of aspartic acid and glutamic acid are also employed. The surface of the substrate usually contains groups that are reactive and can directly be used for attachment to the multimeric biopolymer. In some cases, however, the surface of the substrate needs to be activated to introduce reactive groups for attachment. A number of surface modifying reactions are commonly employed, and include the use of diazo, glutaraldehyde, cyanogen bromide, carbodiimide, epoxide, and 2-fluoro-1-methylpyridinium tosylate. Upon activation of the substrate surface, the multimeric biopolymer is then directly attached through the amine, thiol, or carboxylic groups present in the multimeric biopolymer. Additionally, multimeric biopolymers polymer may be attached to the substrate by introducing complementary affinity pairs into both polymers. For example, the biotin/streptavidin system mentioned in the case of the immobilization of the oligonucleotides to the redox surface is also employed here. Biotin and streptavidin can be attached to the multimer and substrate by well-established chemical/biochemical protocols. The biotin/streptavidin system is not the only one suitable for this type of attachment, and other types of affinity pairs can also be employed.

The polymeric aptamers can also be attached to a surface of the substrate by one of the many methods found in the literature to attach nucleic acids.

When the multimeric biopolymer is blended or attached to a redox polymer which is in electrical contact with a conductor, e.g. a metal or carbon electrode, the protons generated at the redox polymer through electrochemical action are released closer to the multimeric biopolymer to affect the three-dimensional structure thereof. Generally speaking, it is preferable to have more than one means of controlling the actions of a device. This is especially true in the case of medical devices, where the need to ensure safety and efficacy inevitable requires some backup control system that is externally accessible and able to override the chemical control system if the device is not functioning properly or its actions are no longer appropriate to the needs of the patient. Such a backup system for the present devices may be illustrated through the rigid channel example, with the addition of an element of electronic control through use of redox polymer. The main benefit of this approach is the ability to use the external electrochemical potential to override the chemical actuation. The overriding can result in either a permanent change in the structure of the multimeric biopolymer (desirable in cases where the system needs to be shut off, for example when a device begins to fail), or in a reversible change of the three-dimensional structure of the multimeric biopolymer. The latter is important when a binding event needs to be reversed for resetting the device. An additional benefit of the "wired" system is the speed by which this electrochemically-induced changes can be imposed on the multimeric biopolymer/redox polymer blend.

The electronic backbone is typically a redox polymer such as polypyrrole, polyaniline, polythiophene, etc. The redox polymer may be deposited by electrodeposition from a solution comprising the precursors thereof onto a conductor surface such as a patterned metal electrode thereby confining the actuator onto the conductive parts of a MEMS or NEMS structure only. The multimeric biopolymer may be lithographically patterned silk screened or drop delivered onto the metal electrode. Preferably, the device further comprises a small battery, a microprocessor (ideally incorporating telemetry), and a storage chamber for holding substance which is dispensed when an analyte binds to the multimeric biopolymer. For devices which are used to deliver therapeutic compounds such as for example a drug, it is preferred that the device be implantable and be comprised or coated with a biocompatible substance.

The device can further comprises an override system which comprises a hydrogel/redox polymer blend instead of just a redox polymer. This allows coupling of the binding event with swelling/shrinking of the hydrogel while maintaining the override of the chemical actuation by an external chemical potential. The redox polymer may be seen as a conductive electrode extending throughout the hydrogel. The major benefit is that ionic changes induced by a potential change on the metal electrode are now distributed throughout the hydrogel making for a faster response of this mixed conductor system. The mechanism of swelling and shrinking remains the same as with the hydrogel on a metal electrode except that the effect is faster and can permeate through a thicker layer of hydrogel. Moreover the effect is not necessarily based on a pH change. For example, the effect may be based on water uptake by the hydrogel.

The redox polymer can be electrodeposited on the conductor with the gel film already in place. A hydrogel is permeable to the monomers of a redox polymer so the hydrogel may be placed over the metal electrode and with the electrode biased properly the monomer polymerizes within the overlaying hydrogel. Alternatively the hydrogel and the redox monomers may be mixed beforehand and polymerized in situ on the metal electrode. The redox-polymer/hydrogel blend may then be further modified chemically by incorporating a multimeric biopolymer using any of the chemical attachment schemes discussed above.

Hydrogels

Figure 4:
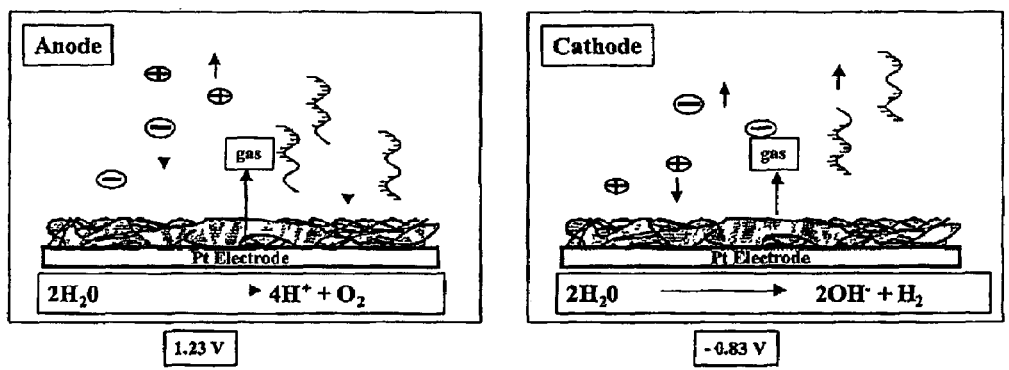
FIG. 4 is an illustration of hydrogel deposited on a metal electrode (e.g., Pt) as an actuator, showing water hydrolysis and reversible swelling and shrinking of the hydrogel.

Hydrogels of the present invention exhibit dramatic effects of swelling and shrinking upon a stimulus. One such stimulus is movement or conformational change of the multimeric biopolymers. Another type of stimulus occurs when there is a change in pH in the environment in which the hydrogel is present. Such local pH change causes water and counter-ions to move in or out of the hydrogel and this induces swelling or shrinking of the hydrogel. This process is illustrated in FIG. 4, where a metal electrode underneath a hydrogel, causes hydrolysis and a local pH change.

Certain types of hydrogels undergo abrupt changes in volume in response to changes in pH, temperature, electric fields, saccharides, antigens and solvent composition. Natural and artificial hydrogels may also be forced to shrink or swell by applying a bias on a metal electrode underneath or embedded in a hydrogel gel. The process is illustrated in FIG. 4 for the case of a hydrogel on top of a Pt electrode. The hydrolysis process creates a local pH change, which changes the volume of the hydrogel. In this case, the hydrogel acts an ionic type actuator, i.e., the polymer does not conduct electrons and actuation is induced by ion migration (somewhat similar to the way an action potential in a nerve cell is generated). The local pH change leads to a different charge on the polymer backbone and this causes water and counter-ions to move in or out of the hydrogel bulk and this, in turn, induces swelling or shrinking of the hydrogel. Depending on the type of hydrogel, a pH increase or pH decrease may induce the hydrogel volume changes. With the metal electrode used as an anode the pH decreases, and with the electrode used as a cathode the pH increases. This swelling behavior is governed by the amount of cross-linking of the hydrogel and the affinity of the polymer chains for solvent.

A hydrogel can be prepared using any suitable monomer that, when polymerized, forms a hydrogel. Such monomers include, but are not limited to, acrylates, acrylamides, acetates, acrylic acids, vinyl alcohols, and glycols. A hydrogel made from an acrylamide can be prepared by combining specific volumes of a filtered 40 wt % acrylamide solution, a 0.1-10 wt % N,N-methylenebisacrylamide solution, and a 98 wt % 2-(dimethylamino) ethyl methacrylated (DMAEMA) solution. The mixture may be deoxygenated by bubbling $N_2$ through the mixture for 15 minutes. A volume of 10-20 µL of a 10 wt % potassium persulfate solution may then be added to initiate the polymerization reaction. A hydrogel can be made from a hydroxyethyl methacrylate (HEMA). A HEMA based hydrogel may be a copolymer of HEMA and methylmethacrylate (MMA) and may be prepared by combining a co-monomer feed of 75 mol % HEMA and 25 mol % MMA, with 1 mol % ethylene glycol dimethacrylate (EGDMA) as the cross-linking agent and a trace amount of dimethoxy phenyl acetophenone (DMPA) as the photoinitiator. The polymerizations are carried out at ambient conditions. Three different compositions of a HEMA-DMAEMA copolymer may be prepared. The first may consist of 0.198 HEMA, 0.0494 DMAEMA, and 0.0752 $H_2O$. The second may be composed of 0.198 HEMA, 0.0494 DMAEMA, 0.00220 EGDMA, 0.450 $H_2O$ and 0.300 ethylene glycol. The compositions above are all in volume fractions. The third PHEMA-DMAEMA composition may be 76 wt % HEMA, 10 wt % DMAEMA, 2 wt % EGDMA, 12 wt % $H_2O$ and a trace amount of DMPA.

Hydrogels can be placed in close proximity to the multimeric biopolymers, or can be blended with multimeric biopolymers, in such a way that the stimulus for swelling or shrinking of the hydrogel is provided by the associated multimeric biopolymer when such biopolymer binds to a specific analyte. The stimulus that causes swelling or shrinking of the hydrogel can be the movement or conformational changes that occurs in the multimeric biopolymer. In this case, the multimeric biopolymer directly causes the swelling or shrinking of the hydrogel.

The binding of an analyte by the multimeric biopolymer can also result in release or consumption of protons. Such protons can cause a local change in the pH and can cause swelling or shrinking of the hydrogel due to movement of water and counter-ions into or out of the hydrogel, as described above.

The present invention is directed to stimuli-responsive hydrogel is prepared by combining a biopolymer having a biomolecule ligand with a monomer capable of forming a hydrogel to form a mixture which is then polymerized to form a porous hydrogel network that integrates the biological recognition element within the hydrogel network. The biological recognition element is a binding protein. For example, the integration of calmodulin (CaM) and its ligand such as a phenothiazine derivative, within a porous hydrogel network causes the hydrogel to undergo a phase transition in the presence of free ligand. This phase transition creates a swelling of the hydrogel network that can be used to trigger the release of the phenothiazine through microactuation or for high-throughput drug screening. CaM has four $Ca^{++}$ ligand binding sites in its structure and is a calcium binding protein that undergoes a large conformational change upon binding calcium, certain peptides, and the phenothiazine class of drugs. Genetically modified CaM monomers have been immobilized in conjunction with phenothiazine derivatives within an acrylamide polymer network. The volume of the hydrogel changes when the non-covalent crosslinking between the CaM and phenothiazine is released due to competitive binding of free chlorpromazine (CPZ) in the binding sites on CaM. The observed hydrogel microdome swelling correlates to the amount of free analyte ligand and can be used in developing 1-D and 2-D microdome sensor arrays for high-throughput screening of pharmaceuticals.

CaM is genetically engineered to contain a unique cysteine at the C-terminus in order to achieve oriented immobilization within the polymer network of the hydrogel. CaM undergoes a large conformational change upon binding calcium and with biomolecules such as peptides and the phenothiazine family of drugs, i.e., chlorpromazine, thioridazine, trifluoperazine and perphenazine.

Figure 5:
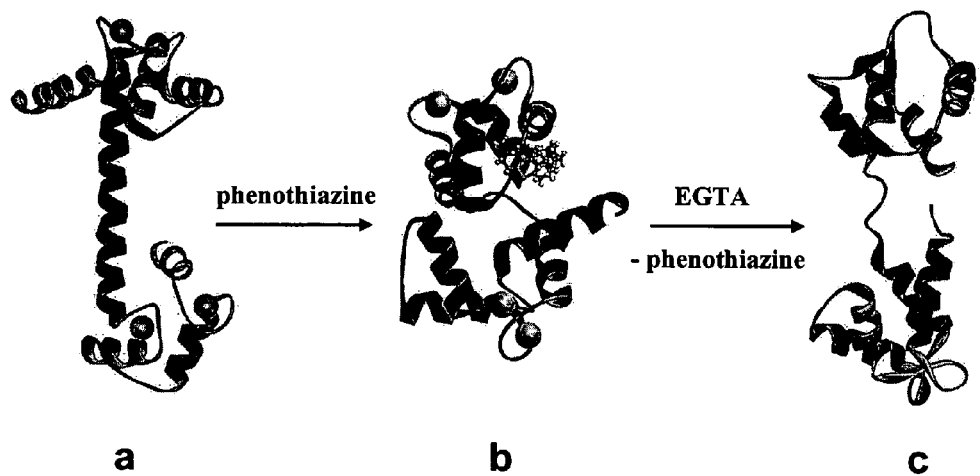
FIG. 5 illustrates (a) the "dumbbell" conformation of calmodulin containing $Ca^{++}$, (b) the conformation of calmodulin in the presence of a phenothiazine, and (c) the conformation of calmodulin in the presence of ethylene glycol-bis(β-aminoethyl ether)-N',N',N',N'-tetraacetic acid (EGTA)

CaM undergoes three conformational changes as illustrated in FIGS. 5(a) to 5(c). The first change is in the presence $Ca^{++}$. In this conformation, CaM has "dumbbell" conformation (FIG. 5(a)). When CaM is bound to phenothiazine, a contrictive conformation (FIG. 5(b)) is formed. When $Ca^{++}$ is removed from CaM using ethylene glycol-bis(β-aminoethyl ether)-N',N',N',N'-tetraacetic acid (EGTA), the protein changes from its bound conformation to its native conformation (FIG. 5(c)) and the hydrogel swells and the phenothiazine is released. The hydrogel of the invention can be used as a biosensor to sense the presence of an analyte, as an actuator to actuate a mechanical response when exposed to an analyte to cause release of a ligand bound to CaM, or to perform both functions, or as a high-throughput screening device.

To integrate a protein such as CaM into the hydrogel network, as described above, the protein is genetically engineered to contain a single cysteine at the C-terminus that allows for the incorporation of an allyl group through its sulfhydryl moiety onto the CaM for polymerization using a maleimide linker. This is accomplished by providing a heterobifunctional linker such as N-(β-maleimidopropyloxy) succinimide ester having a succinimide end and a maleimide end. The allyl group such as allylamine is attached to the succinimide end of the linker while the maleimide end of the linker is attached to the free sulfhydryl group on CaM. The phenothiazine derivative contains a free amine that is able to also react with the heterobifunctional linker. The phenothiazine compound is attached to the succinimide containing an acrylamide moiety. The phenothiazine is immobilized within the CaM and non-covalently bound to the CaM protein, thus creating additional crosslinking within the hydrogel network.

To verify whether the hydrogel responded to a stimulus in the absence of protein, a hydrogel was synthesized that did not contain CaM or its binding ligand. This "control" hydrogel exhibited a swelling response because of the change in ionic strength of the medium. The "control" hydrogel swelled when the ionic strength was increased upon addition of a $Ca^{++}$ salt to the test solution. Upon removal of $Ca^{++}$ from the system, the ionic strength was lowered creating a reversible swelling of the hydrogel network, returning to its original size. This observed ionic strength dependence is an inherent property of hydrogels. It should be noted, however, that the protein-integrated hydrogel shrank in the presence of $Ca^{++}$ while the "control" hydrogel swelled under the same conditions. Hence, the protein-integrated hydrogel did not only swell reversibly, but also overcame the inherent shrinking expected as a result of the change in ionic strength.

The protein-integrated hydrogel can also be responsive to analytes such as drugs or pharmaceutical compounds. For example, a CaM-integrated hydrogel can be responsive to the phenothiazine class of drugs. The hydrogel can swell when chlorpromazine (CPZ) is integrated into the hydrogel polymer network because immobilized phenothiazine is displaced from CaM by free CPZ. Phenothiazine is released from its CaM binding site and replaced by CPZ creating a relaxation of polymer chains. This relaxation allows more water to permeate the porous hydrogel polymer network, thus hydrogel swelling occurs. In the absence of free CPZ, the hydrogel will shrink as the phenothiazine is re-bound to the CaM in the presence of $Ca^{++}$, returning to its original size. Placement of the CaM-integrated hydrogel in fresh $Ca^{++}$ buffer solution containing no CPZ caused the hydrogel to return to its original state and the phenothiazine became re-bound to the CaM.

Figure 6:
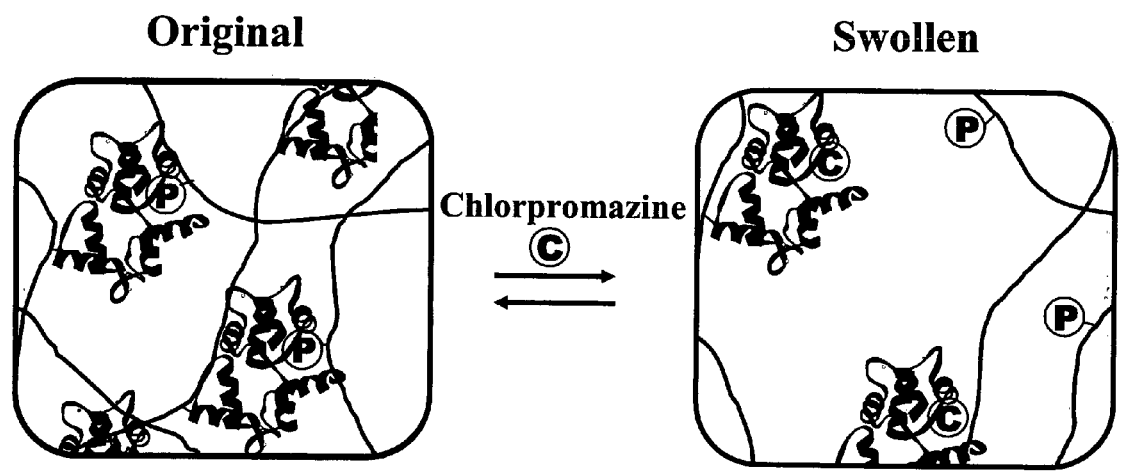
FIG. 6 illustrates the hydrogel structure of the original and swollen states of the calmodulin integrated hydrogel in the presence of chlorpromazine.
Figure 7:
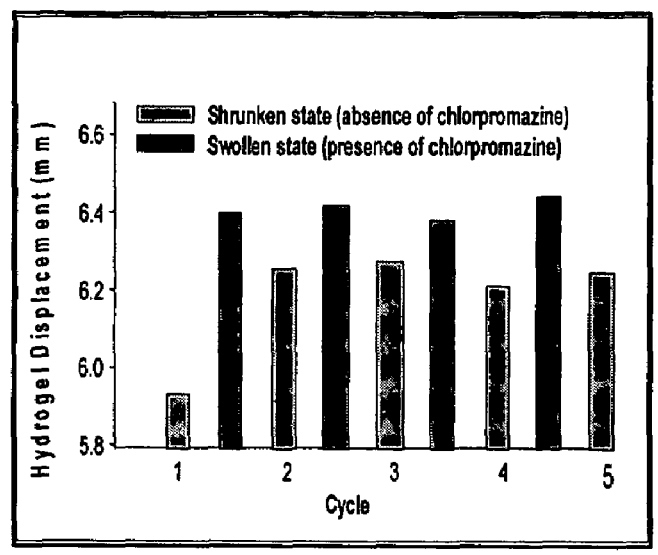
FIG. 7 graphically illustrates the swelling and shrinking of the camodulin protein integrated hydrogel in the presence and absence of chlorpromazine through 5 cycles.

The reversible swelling of the hydrogel can be seen in FIG. 6. In the first stage, CaM is bound to a phenothiazine. In the presence of CPZ, competitive binding occurs, and the non-covalent crosslinking is released creating expansion of the hydrogel network. The fact that CPZ was able to displace the phenothiazine from the CaM binding site is due to the fact that CPZ has a higher binding affinity for CaM than phenothiazine. FIG. 7 shows the swelling and shrinking of the CaM protein integrated hydrogel in the presence and absence of CPZ through 5 cycles.

A number of proteins (e.g., enzymes, antibodies, binding proteins, etc.) demonstrate very specific recognition toward their ligand molecules, which in nature, among others, translates into the production of physiologically important compounds, transport of molecules, and immune response. It is well established that one can take advantage of the above-mentioned interactions between a particular ligand and its protein counterpart in a number of biomedical applications such as in the biosynthesis of biomolecules and pharmaceutical compounds, the development of immunoassays, etc. Protein-based biomolecular recognition events are typically accompanied by a protein conformational change upon binding to the corresponding target ligand. These changes can be classified as hinge or shear motions and can be significant in size, up to several angstroms. Examples of the proteins that can be integrated into the hydrogel polymer is not limited to calmodulin. Table 1 sets forth examples of such binding proteins with their specific ligands.

TABLE 1

| Class of Binding Protein | Biopolymer | Ligand | Physiological Importance |
|---|---|---|---|
| Calcium-Binding Proteins | Calmodulin | Peptides | Secondary messenger |
| Periplasmic Binding Proteins | Glucose-binding protein | Glucose | Glucose detection, diabetes management |
| Fatty-Acid Binding Proteins | Liver fatty-acid binding protein | Fatty acid | Diabetes, obesity |
| Vitamin-Binding Proteins | Vitamin $B_{12}$ binding protein | Vitamin $B_{12}$ | Pernicious anemia, gastrointestinal disorders |
| Immunosuppressant-Binding Proteins | Cyclophillin A | Cyclosporin A | Organ transplant, rheumatoid arthritis |
| Receptor-Binding Proteins | Cyclic AMP receptor-binding protein | Cyclic AMP | Cyclic AMP Signaling cascade |
| Other Binding Proteins | Fibronectin | Homo-cysteine | Marker of atherosclerosis |

Figure 8:
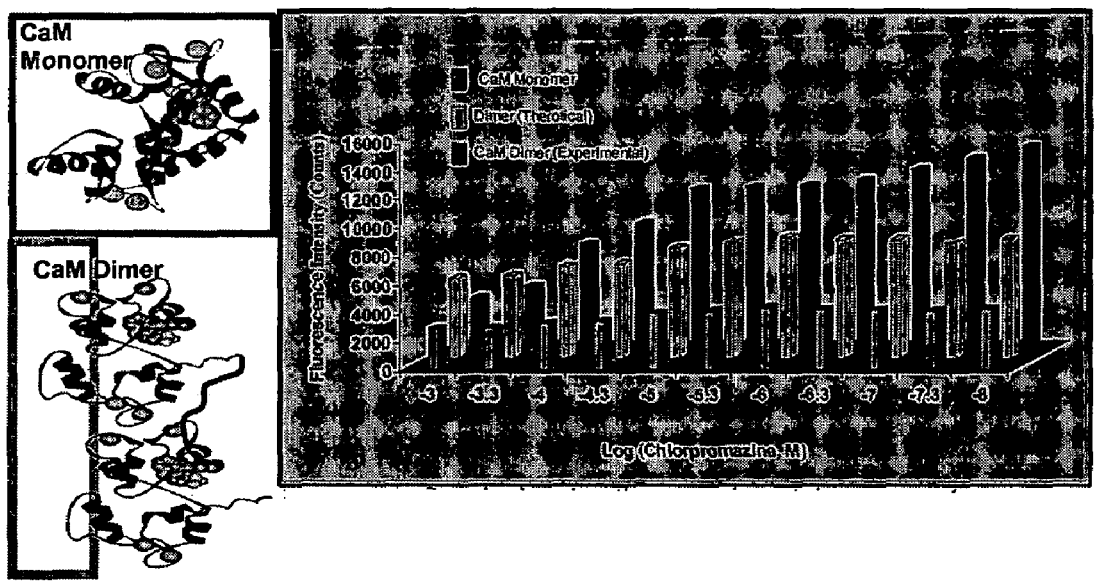
FIG. 8 is a graph showing the experimental response of a camodulin monomer to chlorpromazine, and the theoretical as well as the experimental response of a camodulin dimer to chlorpromazine.

Dimers or multimers of the proteins described above will have larger conformational changes upon binding to their ligand when employed in bioanalytical applications, such as sensing than monomers due to a synergistic effect. For example, a dimer of calmodulin was genetically engineered containing a unique cysteine at position 109 in each of the monomers. An environment-sensitive fluorophore was attached to the protein through the sulfhydryl of the cysteines. The response of the fluorophore labeled dimer in solution to chlorpromazine was determined. The response obtained with the dimer was more than twice that of the monomer, suggesting a synergistic effect (FIG. 8).

Figure 10:
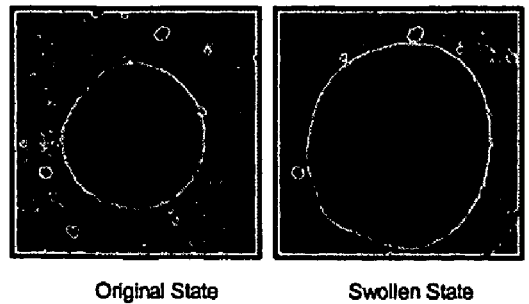
FIG. 10 shows hydrogel microdomes in the original (shrunken) state and the swollen state in response to the presence of chlorpromazine.

The protein integrated hydrogels as described above are used to form a hydrogel microdome or an array of hydrogel microdomes on a substrate. The microdome is illustrated in FIGS. 9(b) to 9(d). FIG. 9 shows SEM images (a) and (c) depicting protein-integrated hydrogel swelling. The SEM images show the pore size of the stimuli-responsive hydrogel with a corresponding ellipsoid surface map in two states: (a) and (b) represent the original (shrunken) state while (c) and (d) represent the swollen state. The microdomes can be used to screen analytes as well as can be used as a biosensor or an actuator. It will be noted that the swelling of the microdome does not affect the diameter as much as it does the height of the microdome. FIG. 10 shows photographs of the hydrogel microdome in its original (shrunken) state and in its swollen state in response to the presence of CPZ.

A crosslinked CaM-phenothiazine hydrogel mixture containing a photoinitiator is prepared and microdomes are micropipetted onto a polymethyl methacrylate or silanized glass substrate and polymerized in UV light. The glass substrate can be glass slides cut from pre-cleaned Gold Seal microslides. To silanize the glass substrate, the substrate is immersed in a 10% (v/v) solution of 3-(trimethoxysilyl)propyl methacrylate (MPTS)/toluene for 1 hour at 70° C. and then dried. Another method for silanize the glass substrate is to place the substrate in a vacuum desicator containing MPTS at the bottom of the desicator and pulling a vacuum for 1½ hours at room temperature. Still another method of silanizing is to immerse the glass substrate into a silane reagent such as trimethyl chlorosilane (TMS) and dry the substrate. It is important to air dry the glass substrate after silanization to reduce the risk of wiping away the coating on the substrate. As for the a polymethyl methacrylate substrate, it can be treated to make the surface more hydrophilic by the addition of —OH groups and by adding polarity to enhance the adhesion of the hydrogel microdomes formed by polymerizing the mixture.

The mixture forming the hydrogel can contain a crosslinker. The responsive swelling is dependent on the amount of crosslinker and protein used to prepare the hydrogel. For example, hydrogels with 0.1, 0.5, 1, and 2% w/w quantities of MBAA crosslinker relative to acrylamide (AAm) were synthesized and examined. The hydrogel swelling increased by reducing the crosslinker percentage. The hydrogel with 0.1 crosslinker is quite fragile providing very low mechanical stability for the experiment. Varying the quantity of CaM immobilized in the hydrogels prepared with 1% (w/w) crosslinker relative to monomer, hydrogels integrated with CaM quantities of 1, 3, 6, and 9 nmol/100 mg monomer (keeping a 1:1 ratio of CaM:ligand) produced a swelling response. The data suggests that there was a minimum protein quantity of 3 nmol/100 mg monomer needed to achieve a given displacement, and additional quantities of CaM over that threshold had little effect on the overall swelling response of the hydrogel.

Stimuli-responsive hydrogel microdomes are reproducibly synthesized using a "microspotting" technique wherein the microdomes are deposited on a substrate using any dispensing equipment that can provide reproducible microdomes (i.e., substantially the same height, diameter and volume). Although not limited to the following techniques, the microspotting can be accomplished using a micropette, glass capillaries, ink jet printing or by lithographic printing.

The microdomes are prepared by first mixing a binding protein with at least one ligand and a monomer capable of forming a hydrogel. The mixture also contains a crosslinking agent and a radical producing polymerization initiator. The mixture is then applied such as by micropipetting onto a substrate. The substrate is pretreated such that the microdomes are covalently attached to the substrate. A suitable substrate material can be polymethyl methacrylate or silanized glass slides. This is desirable so that the diameter of the microdome does not change drastically upon swelling. If a micropipette is used, the pipette volume size can range from 0.2 µL to 15 µL, or from 0.2 µL to 10 µL or from 0.2 to 2 µL. However, sizes above 1 µL only affect the diameter of the microdome with no substantial change in height of the microdome. The microdomes so formed are then polymerized. The slides can be stored in a humidity chamber, i.e., a covered container containing water, to prevent dehydration of the hydrogel.

Figure 11:
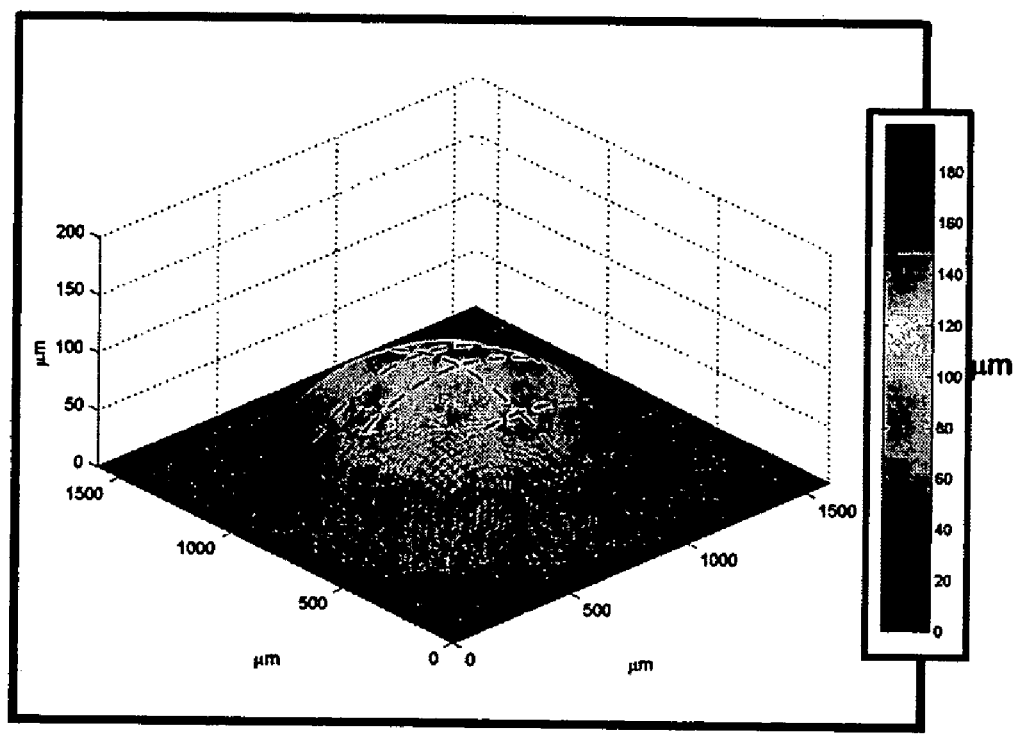
FIG. 11 shows ellipsoid surface map of a hydrogel microdome.
Figure 12:
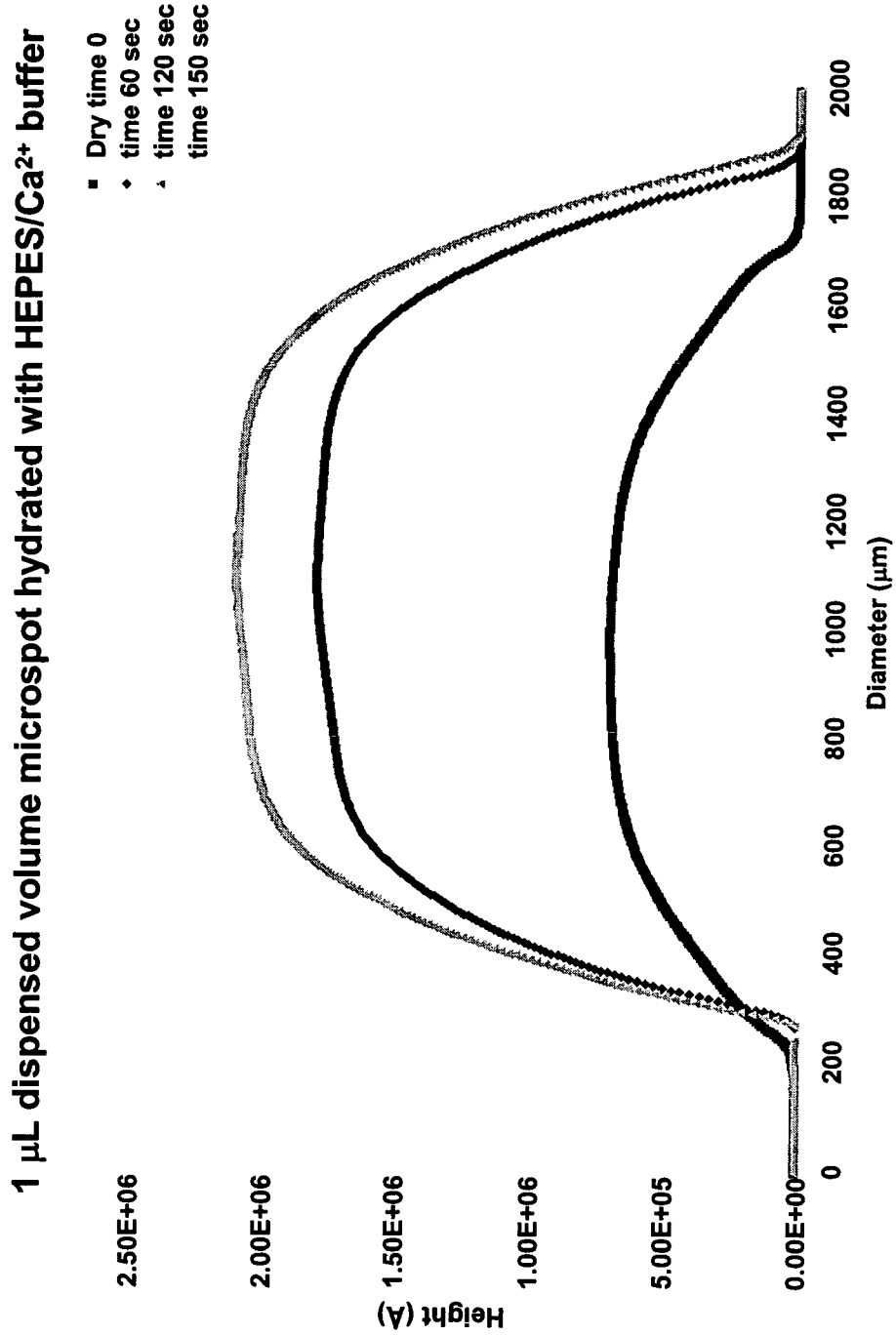
FIG. 12 illustrates graphically the swelling profiles of stimuli-responsive hydrogel microdomes.

FIG. 11 illustrates the microdome. A stylus profilometer such as an Alpha Step 500 surface profilometer (Tencor Instruments, Moimtain View, Calif.) is used to measure the size and volume of the microdome. The profilometer has a fine tip that drags across the surface of the microdome and moves up or down based on the contour of the microdome being profiled. The dashed lines in FIG. 11 indicate surface profiles used in determining surfaces with MatLab v 6.5, which is commercially available mathematical computer program that can perform complex functions such as determining size and volumes of three dimensional surfaces. FIG. 12 illustrates the swelling profile of stimuli-responsive hydrogel microdomes and profiles the height change exhibited by a 1 µL dispensed volume microspot hydrated with HEPES/Ca$^{++}$ buffer after various buffer incubation times.

By using micropipetting techniques, microdomes that are on the order of 800-2000 µm in diameter and 60-120 µm thick can be made reproducibly with high precision. For example, Table 1 below shows a sampling of ten microdomes deposited formed on a substrate from a 1 µL pipette using a commercially available micropipetting equipment (Finnpipette Multchannel model) where the diameter (d) and height (h) of the microdomes were measured and the volume (V) was computed using the formula:

$$V = \frac{1}{2}[4/3(d/2)^2(h)\pi].$$

The data shows consistency in that the relative standard deviation (RSD) of the diameter, height and volume of the microdomes are 4.6%, 6.1% and 8.3%, respectively. Relative standard deviations of 10% or less are acceptable accuracy.

TABLE 2

| Microdome | Diameter (µm) | Height (µm) | Volume (µm$^3$) |
|---|---|---|---|
| 1 | 1123 | 88.04 | 5.81 × 10$^7$ |
| 2 | 1314 | 75.79 | 6.85 × 10$^7$ |
| 3 | 1215 | 89.31 | 6.90 × 10$^7$ |
| 4 | 1247 | 81.29 | 6.62 × 10$^7$ |
| 5 | 1247 | 86.69 | 7.05 × 10$^7$ |
| 6 | 1207 | 82.00 | 6.25 × 10$^7$ |
| 7 | 1271 | 74.63 | 6.31 × 10$^7$ |
| 8 | 1314 | 83.24 | 7.52 × 10$^7$ |
| 9 | 1271 | 86.97 | 7.35 × 10$^7$ |
| 10 | 1287 | 87.01 | 7.54 × 10$^7$ |
| Avg ± SD | 1249 ± 57.4 | 83.5 ± 5.1 | 6.8 × 10$^7$ ± 5.7 × 10$^7$ |
| % RSD* | 4.6% | 6.1% | 8.3% |

Because of the reproducibility of the microdomes using micropipetting techniques, it is not necessary to reprofile the microdomes each time a microdome is formed.

Figure 13A:
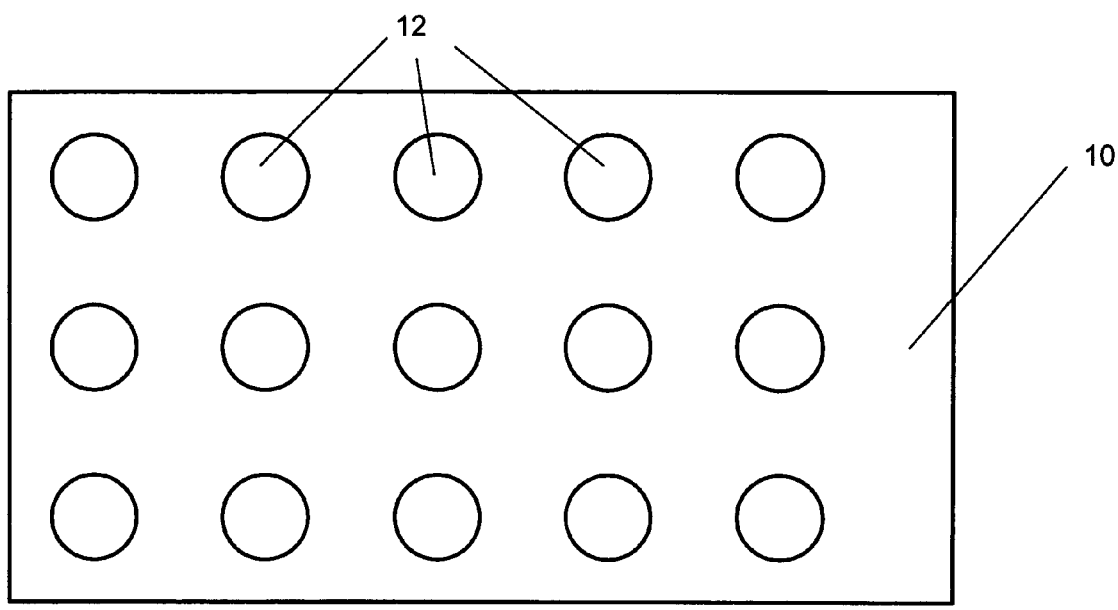
FIGS. 13(a) and 13(b) are plan and side views, respectively, of an array of microdomes on a substrate.
Figure 13:
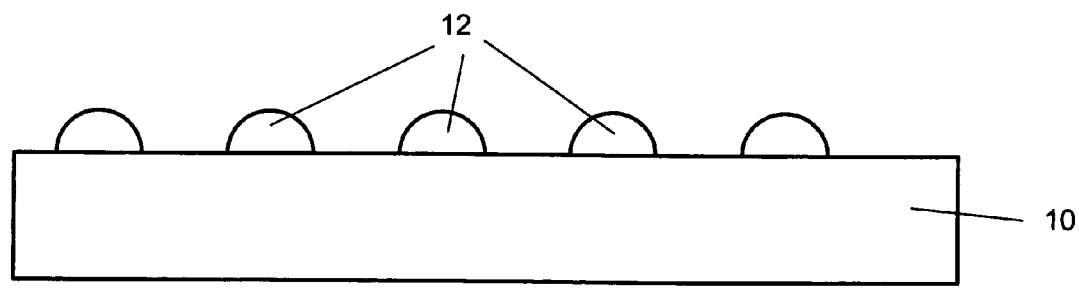

As illustrated in FIGS. 13(a) and 13(b), the hydrogel microdomes 12 can be formed in an array on a substrate 10. Each hydrogel microdome is an ellipsoid. An array of hydrogel microdomes can be formed by pipetting the droplets individually or simultaneously depending on the dispensing equipment employed.

Two types of arrays can be formed. The first array is an individually addressable microdome array. The microdomes in this array are spaced approximately 5 mm to 1 cm apart. With this type of array allows each microdome to be used independently of the others as will be further described below. The second type of array is a collective array which can be used to form a test strip. The micodomes in the collective array are spaced approximately 100 µm to 1000 µm apart. Because the microdomes in the collective array are closely spaced, the microdomes can be deposited in a pattern. By coupling the microdome array with an optical detection system (microscope), a desired pattern can be brought into focus based on the swelling extent of the microdomes (lensing effect). See Serpe et al., "Colloidal Hydrogel Microlenses, *Adv. Mater.*, Vol. 16, No. 2, 184-187 (2004). Also, with this type of arrangement, multiple microdomes comprising different binding protein-hydrogel compositions can be deposited, each composition swelling only if the specific binding ligand is present, forming patterns that may be more or less focussed. With this type of configuration, the presence of an analyte can be visually detected by the focus of the pattern produced by each microdome on the test strip. Thus, a large number of pharmaceutical compounds can be tested.

Figure 14:
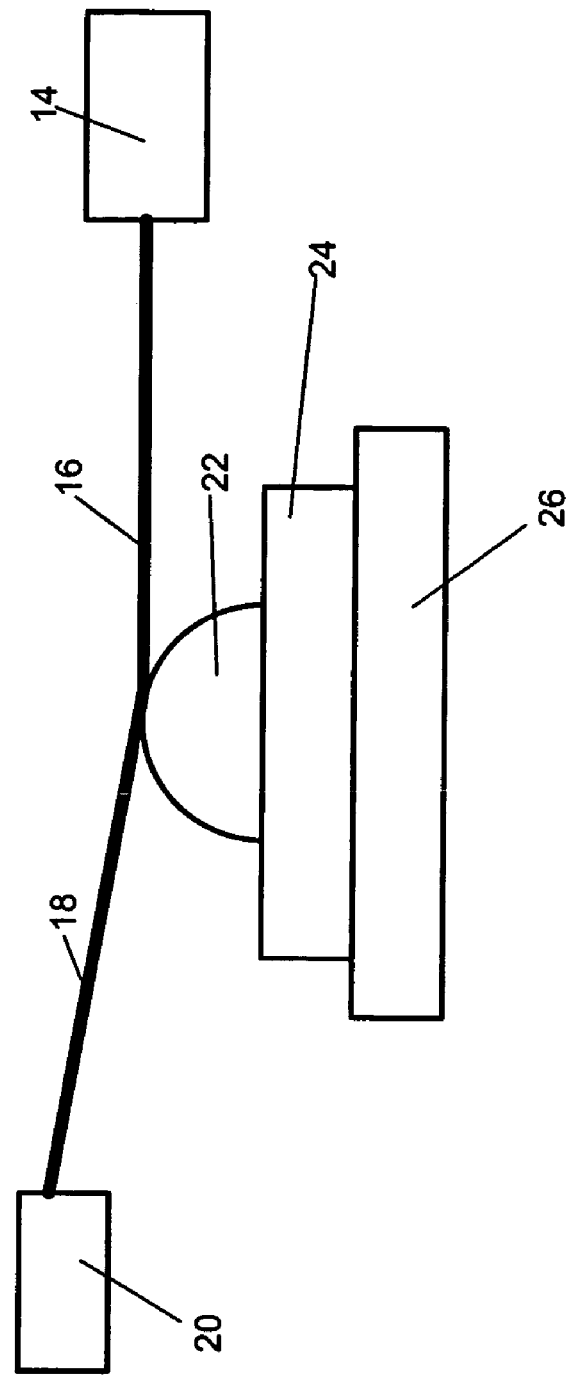
FIG. 14 illustrates the apparatus used to measure the diffraction off the top of a hydrogel microdome.

While the collective array can be used to visually screen for an analyte, the individually addressable microdome array is analyzed using a laser screening system to detect the change in height of the microdomes. The initial size of the hydrogel microdome, including the height of the microdome, is determined using the stylus profilometer. FIG. 14 illustrates an apparatus to measure the height of the hydrogel microdome. The microdome array 22 on substrate 24 is placed on a stage micrometer 26. A light generating means 14 such as a laser diode generates a light beam 16 that is reflected off the top of microdome 22 to produce a diffracted light 18 that is captured by photodiode 20. By positioning the microdome 22 on the stage micrometer 26, the initial height of the microdome can be determined by the amount of light deflected off the top of the microdome 22 by counting the number of photons detected by the photodiode 20. An example of a laser diode interference pattern can be seen in FIG. 15. Upon interference of a swollen microdome, the interference pattern is seen.

After the initial reading, the microdome is not moved. A test solution is applied to the microdome for about 1 to 3½ minutes and then is removed and if the microdome swells, the amount of photons emitted off the microdome will change due to the swelling. The swell time for the hydrogel microdome is about 3½ minutes after the solution is applied to the microdome. FIG. 16 graphically shows the time required for swelling to optimize. If the test solution contains CPZ, the microdome will swell and there will be a change in the height of the microdome. If the test solution does not contain CPZ, there will be no change in the microdome. After the test, the stage micrometer can be adjusted to bring another near by microdome in the array into the sensing area. Swelling of the microdome is observed as a change of height, and not in diameter of the half ellipsoidal structure. The change in height exhibited by the microdomes is proportional to the quantity of the analyte present. For example, FIG. 17 graphically illustrated the swelling response to various CPZ concentrations. The individually addressable microdome array allows for rapid, accurate detection of compounds using individually stimuli-responsive microdomes.

As is evident from the above descriptions, the microdome arrays can be observed in many ways. The arrays can be observed through a microscope, by fluorescence, using a laser system or by measuring refractive index. These are just a few examples observation means that can be used. This list should not be considered all inclusive of observation means that can be employed in this invention.

A potential application of the protein-integrated hydrogel would be as a microactuator for responsive drug delivery systems. For example, a membrane can fabricated from the hydrogel and used to separate a two-chamber cell. Molecules are allowed to permeate through the hydrogel membrane. The profile is monitored as a function of the hydrogel swelling state. Blue dextran (MW 2000 kDa) and vitamin $B_{12}$ (MW 1355 Da) are employed to observe how a stimulus-induced hydrogel swelling controls the molecular transport capabilities of different types of molecules. One chamber of the cell is filled with HEPES/$Ca^{++}$ buffer containing the transport molecule, and the other chamber is filled with HEPES/$Ca^{++}$ buffer solution. The buffer solutions are exchanged for HEPES buffer containing EGTA to trigger the swelling response of the hydrogel. The blue dextran will not pass through the hydrogel in either its swollen or normal (shrunken) stage. This is attributed to its large size. However, transport was observed for vitamin $B_{12}$. The rate of transport can be controlled by the swelling state of the hydrogel. The transport rate is increased by about 2-fold when the hydrogel is swollen by removal of $Ca^{++}$ while the initial transport rate is achieved by returning the hydrogel to its original size. Transport for specific molecules can be tailored by altering the hydrogel crosslinking to create smaller pores. The protein-integrated hydrogel can control molecular transport in two ways by (i) acting as a molecular sieve, which can be fine-tuned to allow only molecules of a certain size to be transported, and (ii) controlling the rate of transport according to the three-dimensional structure dictated by polymer properties and the conformation of CaM.

The ability to control the preset three-dimensional structure of a hydrogel by incorporating a biological recognition element in these stimuli-sensitive biomaterials provided a three-stage swelling response that offered fine-tuned control of hydrogel behavior over conventional hydrogels. The tailored swelling characteristics of the protein-integrated hydrogel can be made to regulate the flow of small molecules in response to an external stimulus for responsive drug delivery applications.

Figure 17:
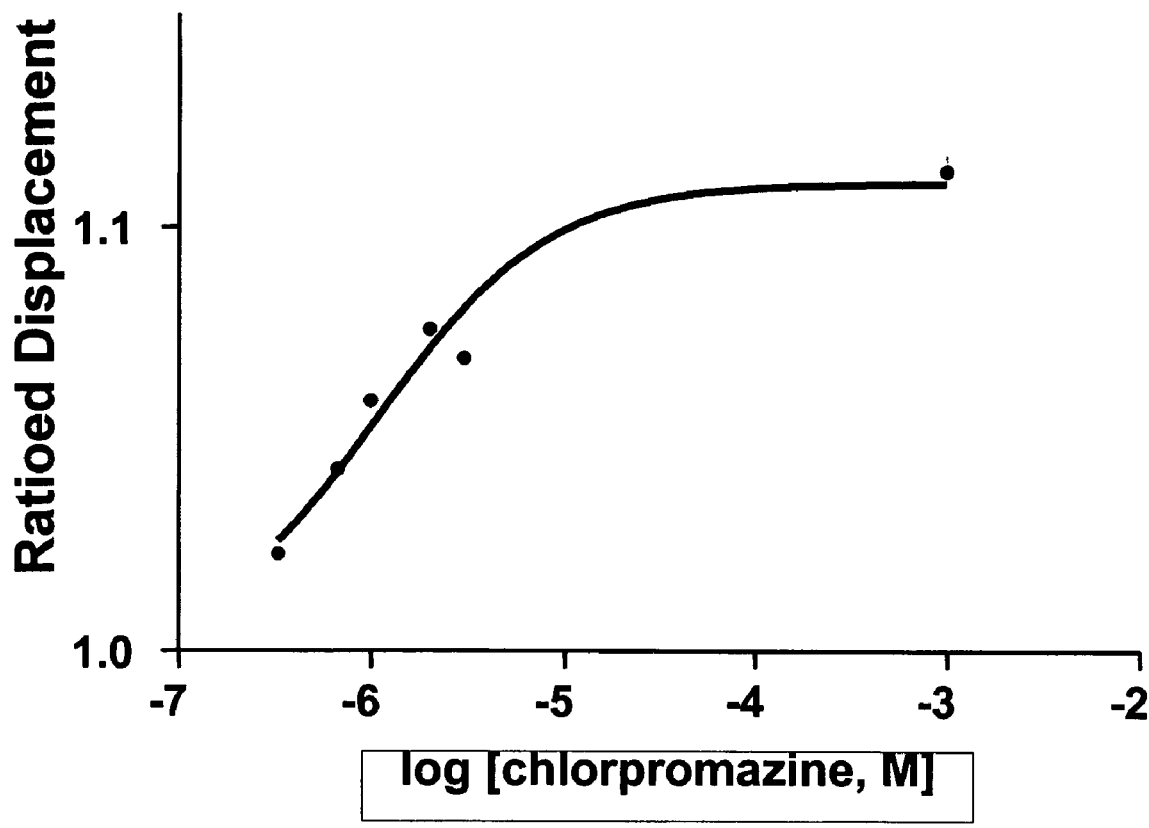
FIG. 17 graphically illustrates the response of the protein and phenyl integrated hydrogel in the presence of chlorpromazine.

To demonstrate application of the protein-integrated hydrogels in the development of sensors, a lower affinity ligand of CaM is incorporated into the hydrogel network. CaM has a lower binding affinity for the phenyl moeity than it does for phenothiazine. Therefore, immobilization of a phenyl ligand with CaM creates an irreversible swelling of the hydrogel in the presence of free phenothiazine and CPZ. The mutated CaM is prepared in the same manner with a unique cysteine at the C-terminus. The modification of CaM remains the same, and the hydrogel is synthesized with the same components, except the phenothiazine derivative is replaced with 4-phenyl-1-butene. As illustrated in FIG. 17, there is an irreversible swelling occurring when the phenyl is immobilized in place of the phenothiazine derivative. Initially, the phenyl is bound to CaM prior to hydrogel synthesis. Upon the initial binding to free chlorpromazine, the hydrogel swells since the immobilized phenyl is released creating a relaxation in the polymer network. When the chlorpromazine is removed, the binding affinity between CaM and phenyl is not strong enough to pull the polymer chains closer together in order for the specific binding event to occur, so the hydrogel remains in a relaxed and unresponsive state.

Microdomes of the protein-hydrogel mixture were applied to either polymethyl methacrylate or silanized glass slides and polymerized with a UV or free-radical initiator. The effect of chlorpromazine addition on the microdomes was studied. It was observed that when the microdomes were subjected to the chlorpromazine, swelling occurred. Such a sensor array platform could be employed for high throughput screening of drugs. In addition, the irreversibility of this smart hydrogel may be an example of a single use polymeric valve. This polymer valve is responsive to varying concentrations of chlorpromazine, which could be used to trigger the release of drug up to a certain concentration of analyte and then shut-off.

Figure 18:
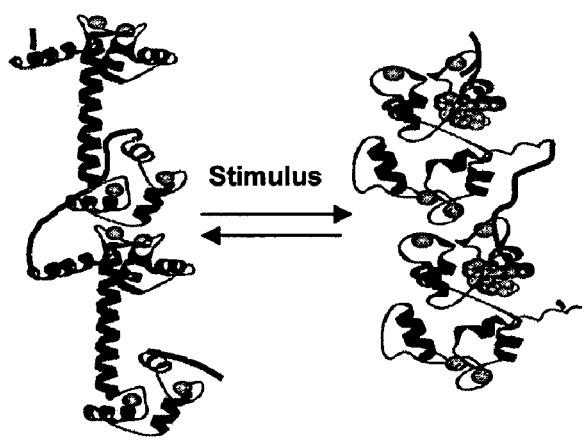
FIG. 18 is a schematic representing a dimer of calmodulin changing conformation in the presence of a stimulus.
Figure 19:
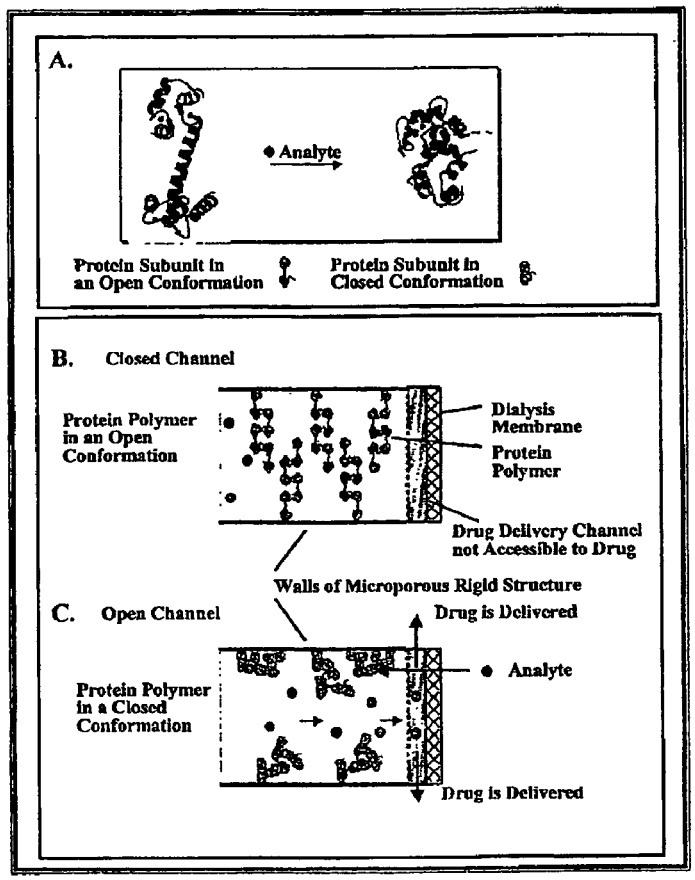
FIG. 19 is an illustration of an example of polymer proteins functioning as sensors and actuators.
Figure 20:
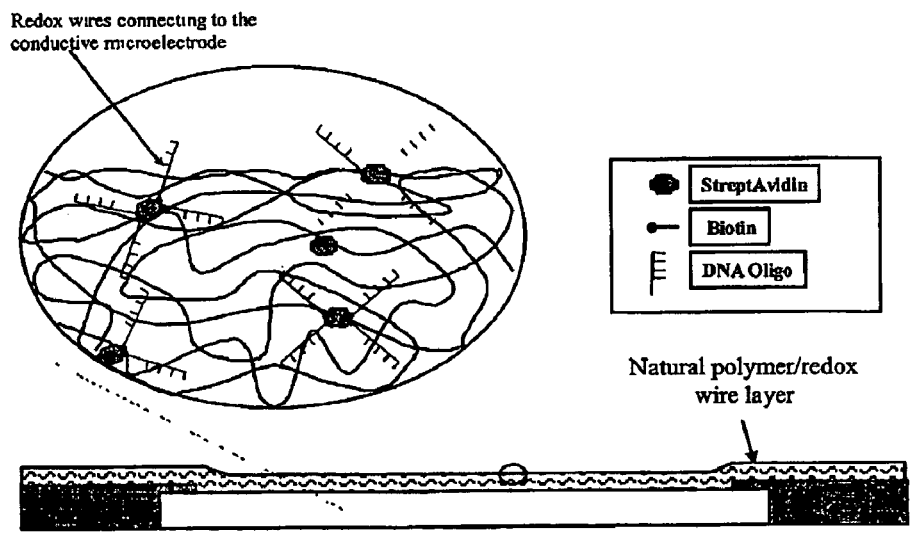
FIG. 20 is an illustration of wiring a multimeric biopolymer (DNA in this case) with a redox polymer to an underlying conductive microelectrode where the DNA is anchored to the redox material via a biotin-streptavidin linkage.

The multimeric biopolymers of the present invention can be used as the foundation of chemical control systems capable of both sensing the presence of a target compound (stimulus) and actuating some mechanical response (FIG. 18). In addition to "sense and respond" applications, these biopolymers could also be used in in vivo drug delivery systems. The multimeric biopolymers will comprise of at least two monomeric units of proteins. When the multimeric biopolymer will be exposed to the stimulus, each monomeric unit will undergo a conformational change. A dimer of CaM responds to a stimulus in a synergistic manner yielding an enhanced response as compared to a monomer or to what theoretically it should be expected from a dimer, i.e., the equivalent of a response corresponding to an additive effect of two CaM monomer molecules.

The hydrogel microdome arrays can be prepared such that they are reusable or disposable. The reusable arrays would be microdome arrays where the swelling of the microdomes can be reversed such as with the reversible swelling that can occur with a phenothiazine immobilized ligand. The disposable arrays have irreversible swelling such as occurs with a phenyl containing ligand.

EXAMPLES

The invention may be better understood by reference to the following examples, which serve to illustrate but not to limit the present invention.

Example 1

Preparation of CaM Protein

The CaM with a unique cysteine at the C-terminus is prepared as follows. The gene for CaM was obtained from the plasmid pVUC-1 using PCR. The CaM gene was modified by site-directed mutagenesis and digested with NdeI and SapI. The digested DNA fragment was ligated into the vector pTWIN-1 to yield the pSD1009 vector. DNA sequencing was performed at the Macromolecular Center (University of Kentucky). Bacteria (*E. coli*, strain ER 2566) were transformed with the pSD1009 vector. Native CaM with a unique cysteine at the C-terminus was expressed using *E. coli* and purified by affinity chromatography with chitin beads (New England BioLabs, Beverly, Mass.). Tris-(2-cyanoethyl) phosphine was stirred with the purified CaM before reaction with the BMPS-allylamine to ensure a free sulfhydro group on cysteine.

Tris-(2-cyanoethyl) phosphine was stirred with the purified CaM before a linker containing a vinyl group was attached to the free sulfhydryl residue on CaM. To accomplish this, the introduced sulfhydryl group on CaM was reacted with a premixed solution of N-[β-maleimidopropyloxy]succinimide ester (BMPS) in dimethylsulfoxide and allylamine in a HEPES, pH 8.0 buffer. The free amine group on the corresponding binding ligand 3-(trifluoromethyl-phenothiazin-10-yl) propylamine was reacted with N-succinimidylacrylate, a linker also containing a vinyl group.

Example 2

Synthesis of CaM-Phenothiazine Hydrogel and Hydrogel Arrays

Protein-integrated hydrogels were synthesized by free-radical polymerization of the modified CaM, vinyl-containing 3-(trifluorometyl-phenothiazin-10-yl) propyamine (TAPP), acrylamide (AAm), and N,N'-methylenebis(acrylamide) (MBAA). TAPP and CaM were preincubated before polymerization, and as a result, immobilized TAPP is non-covalently bound to CaM creating additional crosslinking within the hydrogel network. Modified CaM (3 nmol), vinyl-containing TAPP (3 nmol), acrylamide (AAM) (0.014 mol), N,N'-methylenebis-(acrylamide) (MBAA) (6.5 µmol, 1% w/w AAm), 20 µL potassium persulfate (KPS) (0.1 M), and 40 µL N,N,N',N'-tertramethylethylenediamine (TEMED) (0.4 M) were mixed in 1 mL 10 mM HEPES buffer containing 10 mM $CaCl_2$.

The stimuli-responsive hydrogel microdomes can be reproducibly synthesized using a "microspotting" technique. This technique comprises pipetting 1 µL one or more droplets of a mixture of CaM, TAPP, AAm and MBAA onto a silanized glass substrate and then polymerizing in a nitrogen environment for 2 hours at room temperature to form the hydrogel microdomes. After polymerization, the slides are stored in a humidity chamber, wherein the humidity is to prevent dehydration of the hydrogel.

The glass substrate is silanized by treating the glass slides with the vapor of a MPTS/toluene solution by placing the slides in the bottom of vacuum desicator and pulling a vacuum for 1½ hours.

Example 3

Making of a Calmodulin Dimer Protein

CaM is a calcium-binding protein that also binds phenothiazines. When CaM binds calcium, it undergoes a conformational change. This conformational change allows CaM to interact with CaM binding proteins, peptides, and drugs such as trifluoropiperazine and phenothiazine. Such a conformational change will be larger when single CaM molecules are linked or fused together to yield a polymeric CaM molecule comprised of at least two single CaM molecules. This example describes preparation of a CaM dimer, a single molecule comprised of two single CaM molecules.

A CaM dimer protein is made by fusing two CaM-encoding genes together, end-to-end. Such gene fusion techniques are well known to those experienced in the art. The CaM dimer fusion gene is then cloned into a plasmid that will allow expression of the gene in bacteria. The plasmid is used to transform *E. coli* and bacterial colonies that contain the plasmid are selected. The transformed *E. coli* are grown and the CaM dimer protein is isolated from the cells using standard protein purification techniques well known to those skilled in the art. CaM is then purified using a phenothiazine affinity column, to which CaM binds in the presence of calcium, and is eluted with an EGTA-containing buffer (Hentz and Daunert, 1996, Anal Chem, 68:3939-44.; Hentz, et al., 1996, Anal Chem, 68:1550-5.).

Example 4

Comparison of $Ca.^{++}$ Conformation Changes in CaM Monomer and Dimer Proteins Using the Fluorescence Assay In order to measure the extent of conformation change in CaM molecules in response to calcium and phenothiazine binding, a system has been developed in which a fluorophore is conjugated to a cysteine residue that had been inserted at amino acid 109 of wild type CaM using methods well known to those skilled in the art. This CaM mutant was called CaM109. The fluorescence of the fluorophore increases as the conformation of CaM changes in the presence of calcium.

Since wild-type CaM contains no cysteines, the addition of a cysteine to CaM at a desired position within the protein, allows for labeling of the protein at this position. Such labeling was done using a thiol-reactive fluorescent label called N-[2-(1-maleimidyl)ethyl]-7-(diethylamino)coumarin-3-carboxamide, or MDCC. MDCC was synthesized using methods known to the literature (Corrie, 1990, J. Chem. Soc. Perkin Trans. 1:2151-2152; Corrie, 1994, J. Chem. Soc. Perkin Trans. 1:2975-2982).

The fluorescence response of MDCC-labeled, CaM109 molecules was recorded in the absence and presence of $3 \times 10^6$ M $Ca^{++}$. The $Ca^{++}$ concentration was controlled by EGTA at pH 8.0, and the free $Ca^{++}$ concentrations were calculated using the software program Chelator (Haugland, 1996, Handbook of Fluorescent Probes and Research Chemicals, 6th edition, Molecular Probes, Eugene, Oreg., p. 52). The results showed that the fluorescence intensity of the molecules increased 90% as compared to calmodulin molecules to which calcium had not been added. In addition, when phenothiazine was added to labeled calmodulin molecules that that had already bound calcium, fluorescence was quenched 100%.

CaM monomer and dimer proteins are made by expression in *E. coli* and purified as described in Example 1. These proteins are then separately labeled with MDCC as described in Example 2. The MDCC-labeled calmodulin monomer and dimers proteins are then recorded in the absence and presence of $3\times10^6$ M Ca$^{++}$, as described in Example 2. The results show that increase in fluorescence of the CaM dimer protein is greater than the increase in fluorescence of the CaM monomer protein.

It should be understood that the preceding is merely a detailed description of preferred embodiments. It therefore should be apparent to those of ordinary skill in the art that various modifications and equivalents can be made without departing from the spirit and scope of the invention. All references, patents and patent publications that are identified in this application are incorporated in their entirety herein by reference. The specific examples presented below are illustrative only and is not intended to limit the scope of the invention described herein.

What is claimed is:

1. A stimuli-responsive acrylate hydrogel network comprising a calmodulin biopolymer monomer or multimer, wherein the hydrogel swells upon binding of a phenothiazine compound by the calmodulin biopolymer monomer or multimer.

2. The stimuli-responsive hydrogel network of claim 1, wherein the calmodulin is a monomer or dimer.

3. The stimuli-responsive hydro gel network of claim 1, wherein the calmodulin is a monomer.

4. The stimuli-responsive hydrogel network of claim 1, wherein the stimuli-responsive hydrogel network is a microdome having an ellipsoidal shape.

5. The stimuli-responsive hydrogel network of claim 1, wherein the stimuli-responsive hydrogel network is an array of microdomes having an ellipsoidal shape comprising the biopolymer.

6. The stimuli-responsive hydrogel network of claim 1 wherein the acrylate is hydroxyethyl methacrylate.

* * * * *